(12) United States Patent
Zachariah

(10) Patent No.: US 10,114,929 B2
(45) Date of Patent: Oct. 30, 2018

(54) MATHEMATICAL MUSICAL ORCHESTRAL METHOD FOR PREDICTING CLASSES OF PATIENTS FOR MEDICAL TREATMENT

(71) Applicant: Rutgers, the State University of New Jersey, New Brunswick, NJ (US)

(72) Inventor: Emmanuel S. Zachariah, Highland Park, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 288 days.

(21) Appl. No.: 14/774,177

(22) PCT Filed: Mar. 14, 2014

(86) PCT No.: PCT/US2014/026982
§ 371 (c)(1),
(2) Date: Sep. 10, 2015

(87) PCT Pub. No.: WO2014/152129
PCT Pub. Date: Sep. 25, 2014

(65) Prior Publication Data
US 2016/0055309 A1    Feb. 25, 2016

Related U.S. Application Data

(60) Provisional application No. 61/782,033, filed on Mar. 14, 2013.

(51) Int. Cl.
| | | |
|---|---|---|
| G06F 19/00 | (2018.01) | |
| G01N 33/574 | (2006.01) | |
| G01N 33/68 | (2006.01) | |
| C12Q 1/6886 | (2018.01) | |
| A61B 10/02 | (2006.01) | |
| C12Q 1/6883 | (2018.01) | |
| G06F 3/16 | (2006.01) | |
| G06F 19/18 | (2011.01) | |
| G16H 50/30 | (2018.01) | |

(52) U.S. Cl.
CPC ......... *G06F 19/3431* (2013.01); *A61B 10/02* (2013.01); *C12Q 1/6883* (2013.01); *C12Q 1/6886* (2013.01); *G01N 33/57423* (2013.01); *G01N 33/6893* (2013.01); *G06F 3/165* (2013.01); *G06F 19/18* (2013.01); *G16H 50/30* (2018.01); *C12Q 2600/112* (2013.01); *G01N 2800/52* (2013.01)

(58) Field of Classification Search
CPC ........ C12Q 2600/106; C12Q 2600/118; G06Q 50/22; G06Q 50/24
See application file for complete search history.

(56) References Cited

U.S. PATENT DOCUMENTS

2010/0247580 A1*  9/2010  Coche ............... C12Q 1/6886
                                              424/277.1

OTHER PUBLICATIONS

"The Infrared Frequencies of DNA Bases: Science and Art", S. Alexander, et al., IEEE Engineering in Medicine and Biology, Mar./Apr. 1999 (Year: 1999).*

(Continued)

*Primary Examiner* — Joseph D Burgess
(74) *Attorney, Agent, or Firm* — Licata & Tyrrell P.C.

(57) ABSTRACT

Methods for classifying patients as responders or non-responders to treatment of a disease and predicting recurrence of disease in a patient using audio tunes are provided.

6 Claims, 28 Drawing Sheets

(56) References Cited

OTHER PUBLICATIONS

"The Infrared Frequencies of DNA Bases: Science and Art", S. Alexander, et al., IEEE Engineering in Medicine and Biology, Mar./Apr. 1999.*

Carr et al. "A systematic review of music therapy practice and outcomes with acute adult psychiatric in-patients" PLoS One 2013 8:e70252.

Ein-Dor et al. "Thousands of samples are needed to generate a robust gene list for predicting outcome in cancer" Proc Natl Acad Sci USA 2006 103:5923-5928.

Gordon et al. "A prognostic test for adenocarcinoma of the lung from gene expression profiling data" Can Epidemiol Biomarkers Prev 2003 12:905-910.

Kalia M. "Personalized oncology: recent advances and future challenges" Metabolism 2013 62:S11-14.

Lee J.S. and Thorgeirsso, S.S. "Genome-scale profiling of gene expression in hepatocellular carcinoma: classification, survival prediction, and identification of therapeutic targets" Gastroenterology 2004 127:S51-55.

Roepman P. "The future of diagnostic gene-expression microarrays: bridging the gap between bench and bedside" Bioanalysis 2010 2:249-62.

Xiang et al. "Microarray expression profiling: analysis and applications" Curr Opin Drug Discov Devel. 2003 6:384-95.

International Search Report and Written Opinion in PCT/US2014/26982 dated Aug. 1, 2014.

International Preliminary Report on Patentability in PCT/US2014/26982 dated Sep. 15, 2015.

\* cited by examiner

KNOWN NON-RESPONDER TUNE 1 (KNRT1)
KNOWN NON-RESPONDER TUNE 2 (KNRT2)
KNOWN NON-RESPONDER TUNE 4 (KNRT4)

FIG. 3C

UNKNOWN TUNE 1 (UNT1/R8)

UNKNOWN TUNE 2 (UNT1/NR5)

| | | | | | | |
|---|---|---|---|---|---|---|
| 50.0 | 5.7 | 6.1 | 5.2 | 5.4 | 5.6 | 5.5 |
| 49.0 | 8.2 | 8.2 | 7.6 | 8.2 | 8.4 | 7.7 |
| 48.0 | 7.0 | 6.6 | 7.4 | 6.6 | 7.2 | 7.8 |
| 47.0 | 4.2 | 4.1 | 3.7 | 4.8 | 3.2 | 4.2 |
| 46.0 | 5.8 | 6.6 | 5.7 | 6.0 | 5.9 | 5.6 |
| 45.0 | 9.4 | 8.4 | 9.3 | 8.4 | 10.2 | 9.8 |
| 44.0 | 8.8 | 8.2 | 9.4 | 8.9 | 8.2 | 9.6 |
| 43.0 | 5.9 | 5.9 | 6.3 | 6.3 | 6.5 | 6.6 |
| 42.0 | 4.9 | 5.5 | 4.4 | 5.7 | 4.8 | 4.7 |
| 41.0 | 4.0 | 4.8 | 3.9 | 4.6 | 4.1 | 4.3 |
| 40.0 | 4.4 | 6.0 | 4.4 | 4.8 | 4.7 | 4.6 |
| 39.0 | 5.4 | 6.4 | 5.1 | 5.6 | 5.8 | 5.1 |
| 38.0 | 3.9 | 3.8 | 3.7 | 5.2 | 3.2 | 3.3 |
| 37.0 | 8.8 | 8.4 | 8.4 | 8.6 | 9.1 | 10.1 |
| 36.0 | 4.9 | 5.3 | 4.4 | 5.4 | 4.3 | 4.3 |
| 35.0 | 6.8 | 8.1 | 6.5 | 7.5 | 7.1 | 7.1 |
| 34.0 | 4.6 | 4.8 | 4.6 | 4.5 | 4.5 | 4.1 |
| 33.0 | 7.2 | 7.8 | 7.3 | 7.5 | 7.0 | 7.3 |
| 32.0 | 3.1 | 3.5 | 2.6 | 3.0 | 2.7 | 2.8 |
| 31.0 | 4.3 | 4.5 | 3.7 | 4.6 | 4.0 | 3.7 |
| 30.0 | 3.8 | 4.3 | 3.8 | 4.7 | 3.8 | 3.8 |
| 29.0 | 5.1 | 4.8 | 4.5 | 5.1 | 4.6 | 5.3 |
| 28.0 | 4.5 | 4.7 | 6.6 | 5.2 | 4.3 | 5.1 |
| 27.0 | 4.4 | 4.5 | 4.5 | 5.2 | 4.8 | 4.3 |
| 26.0 | 5.5 | 6.8 | 5.5 | 6.1 | 5.9 | 5.5 |
| 25.0 | 4.0 | 4.6 | 3.9 | 4.6 | 3.8 | 3.7 |
| 24.0 | 4.0 | 4.3 | 4.0 | 4.4 | 4.0 | 4.0 |
| 23.0 | 11.5 | 11.6 | 11.7 | 11.4 | 11.7 | 11.8 |
| 22.0 | 4.7 | 5.6 | 4.7 | 5.4 | 5.0 | 5.0 |
| 21.0 | 5.6 | 6.6 | 5.5 | 6.1 | 6.1 | 5.2 |
| 20.0 | 8.4 | 7.4 | 7.4 | 7.3 | 7.2 | 7.4 |
| 19.0 | 4.0 | 4.1 | 4.0 | 5.7 | 3.5 | 4.3 |
| 18.0 | 6.5 | 6.3 | 4.9 | 7.7 | 5.7 | 5.8 |
| 17.0 | 5.4 | 6.7 | 5.9 | 6.5 | 5.6 | 6.2 |
| 16.0 | 8.7 | 8.2 | 8.9 | 8.6 | 8.7 | 9.6 |
| 15.0 | 5.5 | 6.7 | 4.7 | 6.6 | 5.4 | 5.4 |
| 14.0 | 7.4 | 8.5 | 7.5 | 8.1 | 8.6 | 8.1 |
| 13.0 | 3.6 | 3.7 | 3.7 | 4.6 | 5.2 | 4.0 |
| 12.0 | 5.6 | 5.9 | 5.8 | 6.1 | 5.6 | 5.0 |
| 11.0 | 6.4 | 6.3 | 5.6 | 6.3 | 7.1 | 5.8 |
| 10.0 | 5.5 | 5.9 | 6.6 | 6.6 | 5.3 | 5.8 |
| 9.0 | 5.0 | 6.2 | 5.1 | 6.4 | 5.0 | 5.3 |
| 8.0 | 3.3 | 5.1 | 3.4 | 4.2 | 3.3 | 3.5 |
| 7.0 | 3.9 | 4.8 | 3.6 | 5.2 | 3.4 | 3.5 |
| 6.0 | 6.2 | 6.5 | 6.1 | 7.8 | 6.5 | 6.2 |
| 5.0 | 6.7 | 7.7 | 6.3 | 6.2 | 7.2 | 7.1 |
| 4.0 | 10.6 | 10.0 | 9.9 | 10.3 | 10.9 | 11.0 |
| 3.0 | 4.3 | 4.8 | 3.9 | 4.3 | 4.4 | 4.3 |
| 2.0 | 4.1 | 6.7 | 4.1 | 4.0 | 3.9 | 3.4 |
| 1.0 | 9.0 | 8.9 | 7.8 | 9.9 | 10.2 | 10.8 |
| Notes | Unknown 3 | Unknown 4 | Unknown 5 | Unknown 6 | Unknown 7 | Unknown 8 |

FIG. 9L

MATHEMATICAL MUSICAL ORCHESTRAL METHOD FOR PREDICTING CLASSES OF PATIENTS FOR MEDICAL TREATMENT

This patent application is the National Stage of International Application No. PCT/US2014/026982 filed Mar. 14, 2014, which claims the benefit of priority from U.S. Provisional Application Ser. No. 61/782,033 filed Mar. 14, 2013, the content of each of which is hereby incorporated by reference in their entirety.

FIELD OF THE INVENTION

The present invention relates to a novel method of predicting classes of patients for medical treatment.

BACKGROUND OF THE INVENTION

Gene expression analysis provides the foundation for studying thousands of individual alterations in gene function. These alterations in mRNA expression can be viewed as biomarkers. Whole genome gene expression assays are routinely used to predict treatment responses in human diseases (Xiang et al. *Curr Opin Drug Discov Devel.* 2003; 6:384-95; and Lee J. S. and Thorgeirsso, S. S. *Gastroenterology* 2004; 127:S51-55). A major limitation with the gene expression data analysis methods is the low prediction accuracy with small sample size (Roepman P. *Bioanalysis* 2010; 2:249-62). Studies have indicated that the prediction accuracy can be increased by increasing the sample size. For example, Ein-Dor et al. reported that ~3000 samples are needed to get good prediction accuracy necessary for the clinical applications in lung cancer (*Proc Natl Acad Sci USA* 2006; 103:5923-5928). It has also been proposed that gene expression data can be supplemented with copy number variation and Single Nucleotide Polymorphism (SNP) information to obtain the accuracy required for class prediction (Kalia M. *Metabolism* 2013; 62:S11-14). Using more than one technique, however, will increase the cost of the test and also the complexity associated with the present data analysis methods.

Currently, a supervised clustering method is used to analyze microarray data to classify a patient for treatment response (Speed, T. (Ed.) 2003 Statistical analysis of gene expression microarray data. Chapman and Hall/CRC, NewYork).

The goal of these approaches is to relate gene expression to different target classes and to use this new information to produce a prediction model. Often, this approach is called pattern recognition. There are many different algorithms, such as linear predictors, neural nets, etc. These are very powerful tools, but each has its own advantages and disadvantages. One would need to know how to select the right method, structure, and definition for a given problem. This approach may not provide accurate results to take clinical decision. For example, a prediction model developed by Gordon et al. could reach only 74% predicting accuracy with ~400 samples; a good outcome but not excellent result (Gordon et al. *Can Epidemiol Biomarkers Prev* 2003; 12: 905-910).

Musical algorithms have been widely used to compose tunes for entertainment purposes. There is a limited usage in medical musical therapy applications (Carr et al. *PLoS One* 2013; 8:e70252).

SUMMARY OF THE INVENTION

The present invention relates to a method of using a mathematical musical orchestral algorithm, referred to herein as MMOA, to predict response of a patient suffering from a disease to a selected treatment for the disease. As demonstrated herein, this novel MMOA is suitable for small sample size with high prediction accuracy.

Accordingly, an aspect of the present invention relates to a method of classifying a patient suffering from a disease as a responder or a non-responder to a selected treatment for the disease.

In one embodiment, the disease is cancer.

In one embodiment, the disease is lung cancer.

This method comprises first analyzing a tissue sample from the patient with a microarray. The data set generated from the microarray is then filtered using a standard microarray data analysis method and an audio tune and/or sound frequency pattern capturing the filtered data from the microarray is then established via the MMOA. The patient is then classified as a non-responder or responder to the selected treatment based upon the assigned audio tune and/or sound frequency pattern being similar to an audio tune and/or sound frequency pattern already previously identified for known responders or known non-responders.

In one embodiment of the present invention, the MMOA is manually operated.

In another embodiment, a web based program converted from the manually operated MMOA and referred to as sound frequency pattern generation and recognition algorithm or SFPGRA is used.

The classification method of the present invention is also useful in predicting recurrence of a disease such as cancer in a patient.

Unless otherwise defined, all technical and scientific terms used herein have the same meaning as commonly understood by one of ordinary skill in the art to which this invention belongs. Although methods and materials similar or equivalent to those described herein can be used in the methods and materials are described herein. All publications, patent applications, patents and other references mentioned herein are incorporated by reference in their entirety. In the case of conflict, the present specification, including definitions, will control. In addition, the materials, methods and examples are illustrative only and are not intended to be limiting.

Other features and advantages of the invention will be apparent from the detailed description, and from the claims.

BRIEF DESCRIPTION OF THE FIGURES

FIGS. 3A through 3F are musical compositions prepared by SFP generation. Normalized gene expression intensity of top 50 biomarkers was converted into musical notes/sound frequencies. A coherent music/SFP specific to each group (FIG. 3A) and patient (FIGS. 3B and 3C) were composed/generated to train the model. Eight data sets were treated as the "unknowns" and the tunes/SFPs were used to validate the model (FIGS. 3D-3F). A double blind test was conducted to test and validate the prediction accuracy of the model. FIG. 3A is an example of a Reference/Theme/Framework tune/SFP specific to non-responders and responders patients composed/generated using non-responders/responders mean value. The tunes/SFPs were used as the reference tunes/SFPs to compose/generate known tunes/SFPs (training set). FIG. 3B shows examples of known non-responder (training set) tunes/SFPs. Three non-responder tunes/SFPs were composed/generated and used as the training set. FIG. 3C shows examples of known responder (training set) tunes/SFPs. Three responder tunes/SFPs were composed/generated and used as the training set. FIGS. 3D-3F show examples of unknown (test set) tunes. Eight tunes/SFPs (4R and 4NR) were composed/generated to validate the MMOA.

FIG. 4A shows the random distribution of microarray signal intensities/numbers. Randomness was observed in the distribution of signal intensities of the top 50 biomarkers obtained by the conventional microarray data analysis. FIGS. 4B and 4C show random distribution of sound frequencies observed in unknown patient 1 data obtained from responder patient 8 and unknown patient 2 data obtained from non-responder patient 5, respectively. Only one patient in each group is shown as an example. Randomness was also observed in the distribution of signal intensities of the top 50 biomarkers after we converted the signal intensities into sound frequencies. FIGS. 4D and 4E show class specific sound frequency patterns of unknown patient 1 data obtained from responder patient 8 and unknown patient 2 data obtained from non-responder patient 5, respectively. A unique sound frequency pattern (SFP) specific to each class was generated after the class specific tunes with the top 50 biomarkers were composed. These patterns were stored in a data base and compared with the SFPs of unknowns to assist in making clinical decisions with respect to a patient. FIGS. 4F and 4G are spectrograms converted from the sound frequency patterns from unknown patient 1 data obtained from responder patient 8 and unknown patient 2 data obtained from non-responder patient 5, respectively, which are useful for further pattern recognition purposes.

In FIG. 7A class prediction was done with top 50 biomarkers specific for surgical treatment response (one parameter). FIG. 7B shows use of the algorithm in subclass predictions such as chemotherapy response or radiotherapy or targeted therapy response in non-responder patients who are eligible for adjuvant chemotherapy or radio or targeted therapy. FIG. 7C shows use of MMOA in the integration of gene expression data with 3-dimensional voxel intensity obtained from computed tomography (CT) scan image data to discriminate malignant nodules from benign nodules in patients at high risk for lung cancer.

FIGS. 9A through 9L provide an example of the wire frames used to develop the web-based sound frequency pattern generation and recognition algorithm (SFPGRA). Tables A through K in Example 1 further describe the numbered elements and type as well as additional notations for the wireframes depicted in FIGS. 9A-9L.

DETAILED DESCRIPTION OF INVENTION AND EMBODIMENTS

Figure 1:
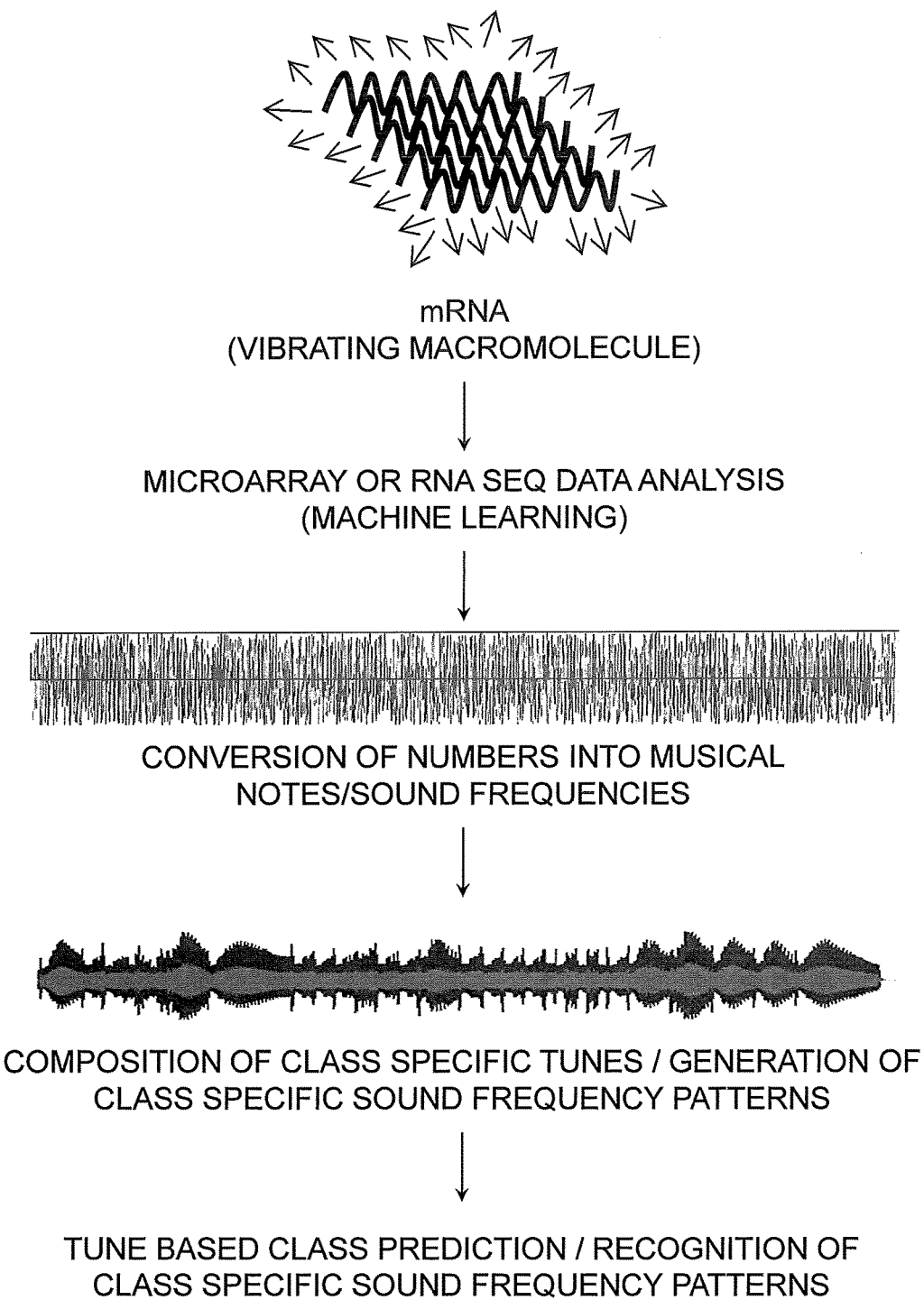
FIG. 1 provides a schematic of the mathematical musical orchestral algorithm protocol used in the method of the present invention for class prediction. In this embodiment of the present invention, mRNA molecules are considered as the vibrating macromolecules and their vibrations/sound frequency patterns (SFPs) are indirectly estimated from a microarray based gene expression analysis. The fluorescent intensity values obtained from DNA microarrays were converted to musical notes/sound frequencies, and the notes were used to compose class specific tunes/SFPs. Patients suffering from cancer are classified into responder or non-responder based on the tunes/SFPs.

Musical algorithms are used widely to compose tunes for entertainment purposes. Usage in medical musical therapy applications has been quite limited.

Since conventional machine learning algorithms cannot achieve the prediction accuracy required in a clinical setting for classifying patients suffering from a disease as responders or non-responders to a selected treatment, in the present invention a mathematical musical orchestral algorithm, referred to herein as MMOA, was integrated into the machine learning process. The MMOA is capable of handling complete gene expression data obtained from whole human genome microarray comprised of ~30,000 human genes. It can be used to analyze more than one clinical parameter such as stage, age, gender and smoking history etc. for class/sub-class predication purposes. It can be also used to predict responses such as, but not limited to, chemotherapy or radiology or targeted therapy response in patients suffering from late stage cancers.

The MMOA can be used for sub-class identification as well. For example, in the first step it can be used to discriminate non-responder from responder after, for example, a surgical treatment. The same algorithm can be used to prediction adjuvant chemotherapy response or radiotherapy or targeted therapy response in non-responder patients who are eligible for adjuvant chemotherapy or radio or targeted therapy.

As shown herein, the combination of mathematical machine learning and MMOA can greatly improve the prediction accuracy of the treatment response in patients suffering from cancer.

In the method of the present invention, a patient suffering from a disease is classified as a responder or a non-responder to a selected treatment for the disease by analyzing a sample from the patient using an RNA, DNA or protein microarray. In one embodiment, if the patient is suffering from cancer, the tumor or a portion thereof is excised from the patient for analysis. Core needle biopsy samples, fine needle aspirations as well as fresh, frozen and formalin-fixed paraffin-embedded tissues samples may also be used.

The data set generated from the microarray is then filtered. An audio tune and/or sound frequency pattern capturing the filtered data from the microarray is then assigned to the patient and the patient is classified as a responder or a non-responder to a selected treatment for the disease based upon the assigned audio tune and/or sound frequency pattern.

The method of the present invention was tested using a Non-Small Cell Lung Cancer (NSCLC) model. At present most of the Stage Ia NSCLC patients are not treated with adjuvant chemotherapy (Qi-Zhu et al. *J Clin Onco* 2010; 28: 4417-4424). Early identification of stage Ia patients likely to recur following surgery will allow the physician to target adjuvant chemotherapy to those patients for whom it is necessary. In stage Ib diseases, most of the patients are treated with adjuvant chemotherapy. However, a subgroup of patients do not recur and hence might not require adjuvant chemotherapy. In stage Ib patients, physician can avoid adjuvant chemotherapy to those who do not require it. Conventional detection and follow-up methods based on the clinical staging and clinic-pathological findings are insufficient to predict recurrence (Sriram et al. *Respirology* 2011; 16: 257-263).

In the present invention, the MMOA was used to convert mRNA signal intensities into musical notes/sound frequencies and class specific tunes/SFPs were composed/generated with the harmonized musical notes/SFPs. By listening and observing the class specific tunes/SFPs, one can discriminate the responders from non-responders of surgical treatment in these NSCLC patients.

While tests were performed on lung cancer patients, as will be understood by the skilled artisan upon reading this disclosure, the method of the present invention provides a simple, sensitive and cost-effective method which can be routinely used in any kind of human disease.

It is important to note that present gene expression data analysis methods considered mRNAs as the inert molecules and use their concentration information (signal intensity) to predict treatment response. In contrast, the present invention considers mRNAs as the vibrating molecules, and uses their macromolecular vibrations/SFPs extracted (from their signal intensity values) for class prediction.

Accordingly, the method of the present invention utilizes what is believed to be the first gene expression algorithm that involves two human senses (i.e. visual and listening) to predict treatment response in human disease. This is believed to also be the first medical laboratory test that uses two human senses for diagnostics applications.

Since the MMOA predictions are based on the tunes/SFPs, it can be effectively used to predict mRNA extracted from Formalin Fixed Paraffin Embedded (FFPE) samples. Even in the absence of some biomarkers, the tunes/SFPs obtained from the remaining expressed genes can be used to identify the clinical outcome of the patient.

The preferred methods and materials are described below in examples which are meant to illustrate, not limit, the invention. Skilled artisans will recognize methods and materials that are similar or equivalent to those described herein, and that can be used in the practice or testing of the present invention.

EXAMPLES

Example 1: Experiments

Figure 2:
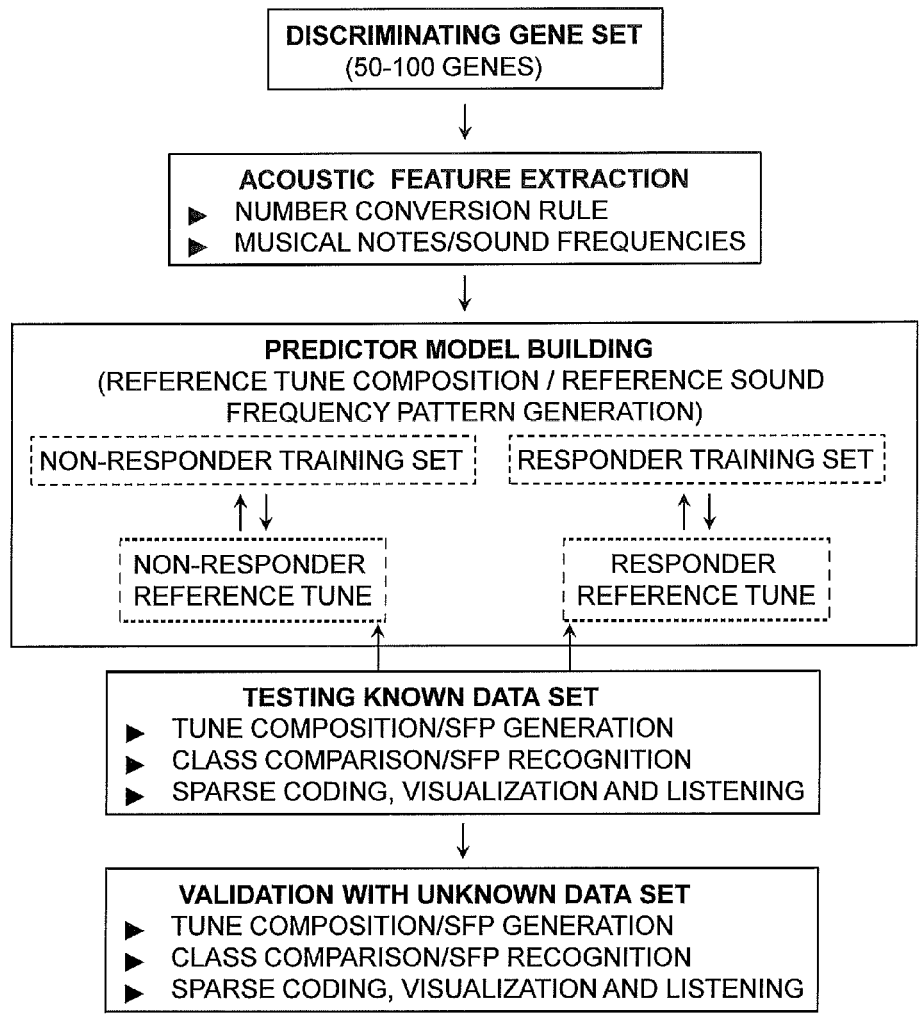
FIG. 2 provides a flow diagram of the steps involved in the development of the class prediction model of the present invention. The model was trained and tested with retrospective clinical samples. The model was built with non-responders and responders training data set and fine-tuned with known test data sets. A double blind test was conducted to test and validate the prediction accuracy of the model.

Conventional gene expression data analysis program uses the concentration/signal intensity information of mRNA to identify the differentially expressed genes for class prediction (Wong et al. *Bioinformatics* 2007; 23:998-1005). In the present invention, an algorithm referred to herein as MMOA was used to convert the signal intensities (numbers) into macromolecular vibrations/sound frequency patterns (SFPs). Class specific tunes/SFPs were composed/generated using coherent music/SFPs. The class specific tune/SFP was used to predict the clinical outcome of unknown patients. The principle of MMOA is shown in FIG. 1. The MMOA was tested and validated using samples obtained from NSCLC patients and showed that this application is central to personalized onco-medicine. The functionality specifications of the class prediction model are shown in FIG. 2.

Comparison with Conventional Microarray Data Analysis

Initially, a conventional microarray data analysis method was used to find out its prediction accuracy. The prediction accuracy of the conventional microarray data analysis was then compared with the MMOA.

Based on the clinical information, patients were classified as a Responder (R) if no recurrence was detected within 5 years after surgery. Otherwise, the patient was considered a Non-responder (NR). Twenty three non-responders and 13 responders were used to build and test the model, and 8 samples were treated as the "unknowns". Total RNA was amplified and hybridized onto human whole genome microarrays (Affymetrix HGU-133 Plus 2.0). The microarray data was normalized using Robust Multi-array Average (RMA) procedure on Affymetrix GeneChip Operating Software (GCOS). For further analysis, the data was filtered and the probes that do not change were removed from the analysis.

Standard clustering procedures (e.g. hierarchical or sammon map) did not group the samples according to their status of responders or non-responders. Also, according to the limma analysis there were no differentially expressed genes between responders and non-responders group. This indicated that the differences between the two groups is more subtle and has to be addressed using more sophisticated and sensitive analysis. Analysis was performed in R statistical language using standard Bioconductor packages and custom-written code (see http: with the extension //bioconductor.org/ of the world wide web).

The classification model was learned on filtered data from responders (R) and non-responders (NR) using penalized regression procedure. The resulting classifier has a leave one out cross-validation accuracy of 0.89. In other words, the error of misclassification in training data is 0.11 implying that 9 out of 10 patients/samples are predicted correctly.

A confusion matrix of the classifier is given by the following:

| Object | True | |
| --- | --- | --- |
|  | NR | R |
| NR | 22 | 3 |
| R | 1 | 10 |

One out of 23 non-responders (NR) 1 was incorrectly predicted, and 3 out of 13 responders (R) were incorrectly classified in a leave-one-out cross-validation procedure.

Classifier built on the training dataset was applied to predict the clinical outcome of the 8 unknown patients.

Mathematical Musical Orchestral Algorithm (MMOA)

Figure 3A:
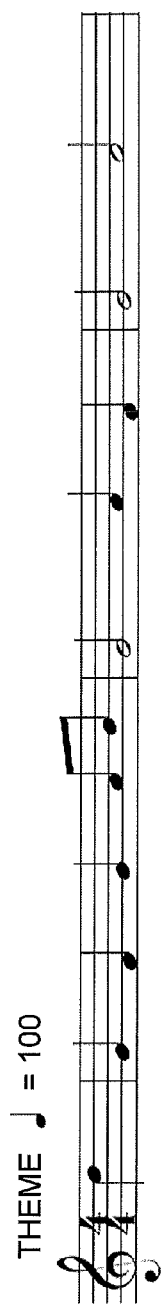
Figure 3A:
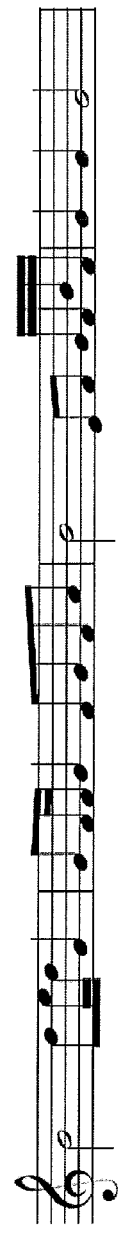
Figure 3A:
Figure 3A:
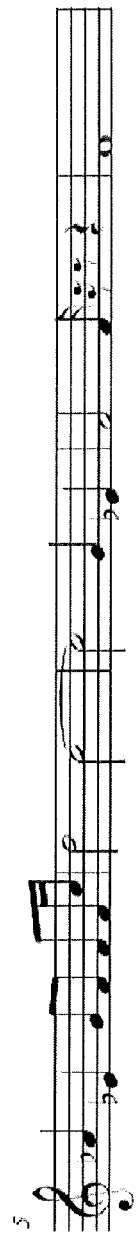
Figure 3B:
Figure 3B:
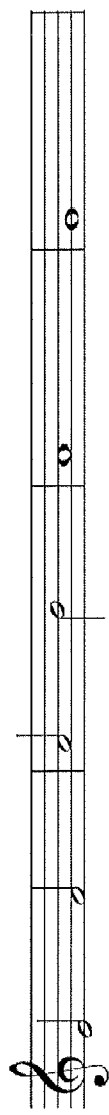
Figure 3B:
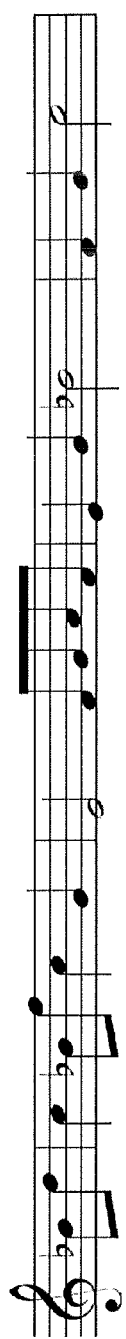
Figure 3B:
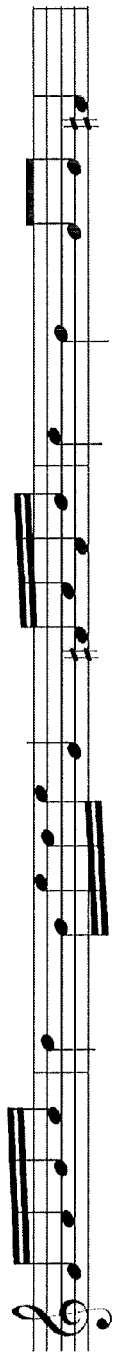
Figure 3C:
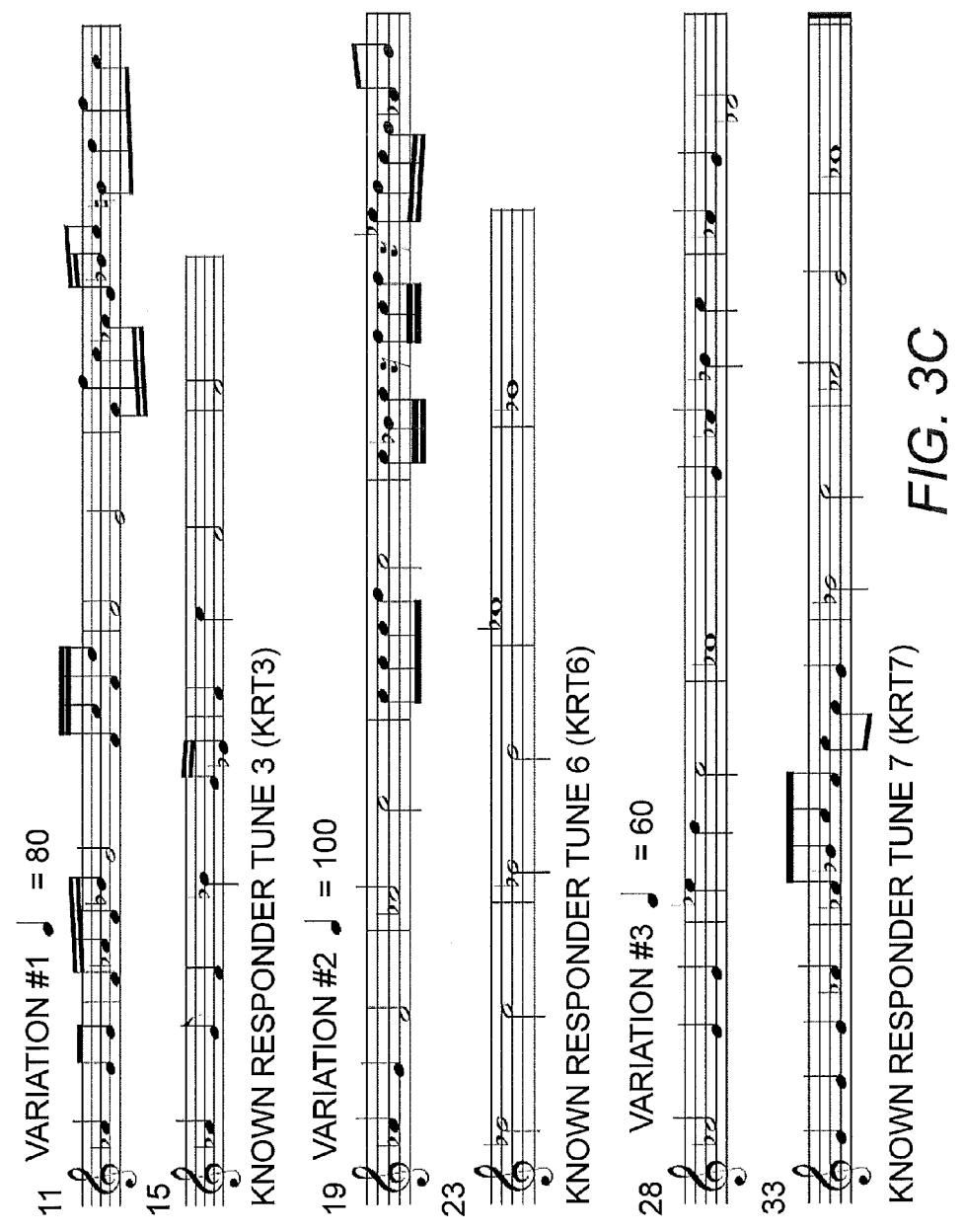
Figure 3D:
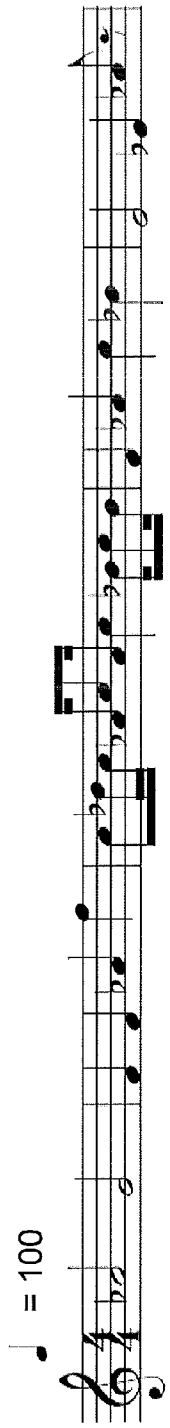
Figure 3D:
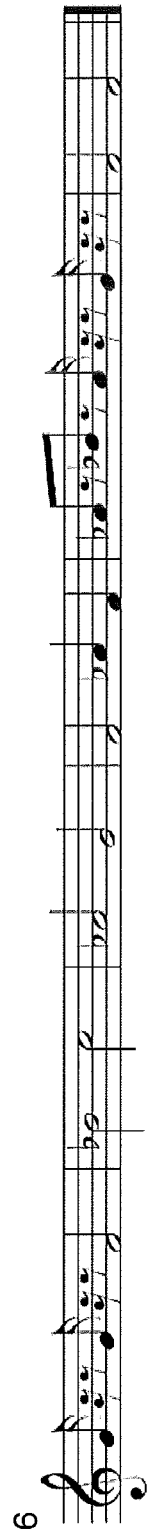
Figure 3D:
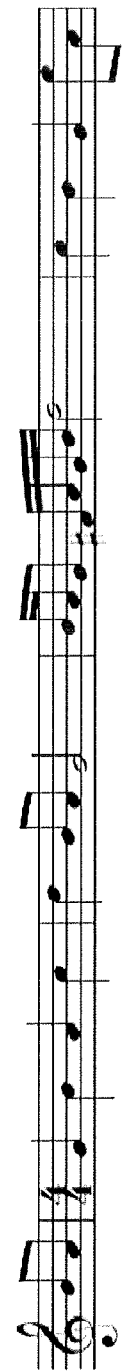
Figure 3D:
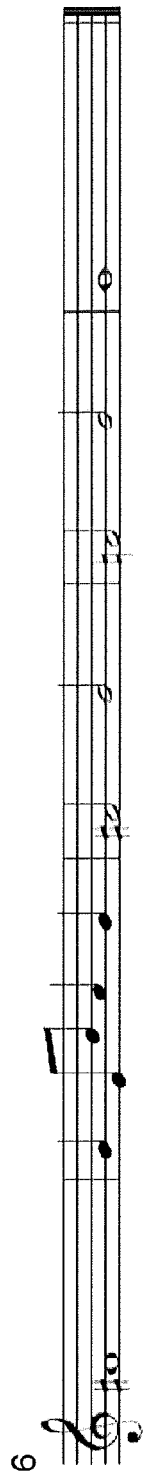
Figure 3E:
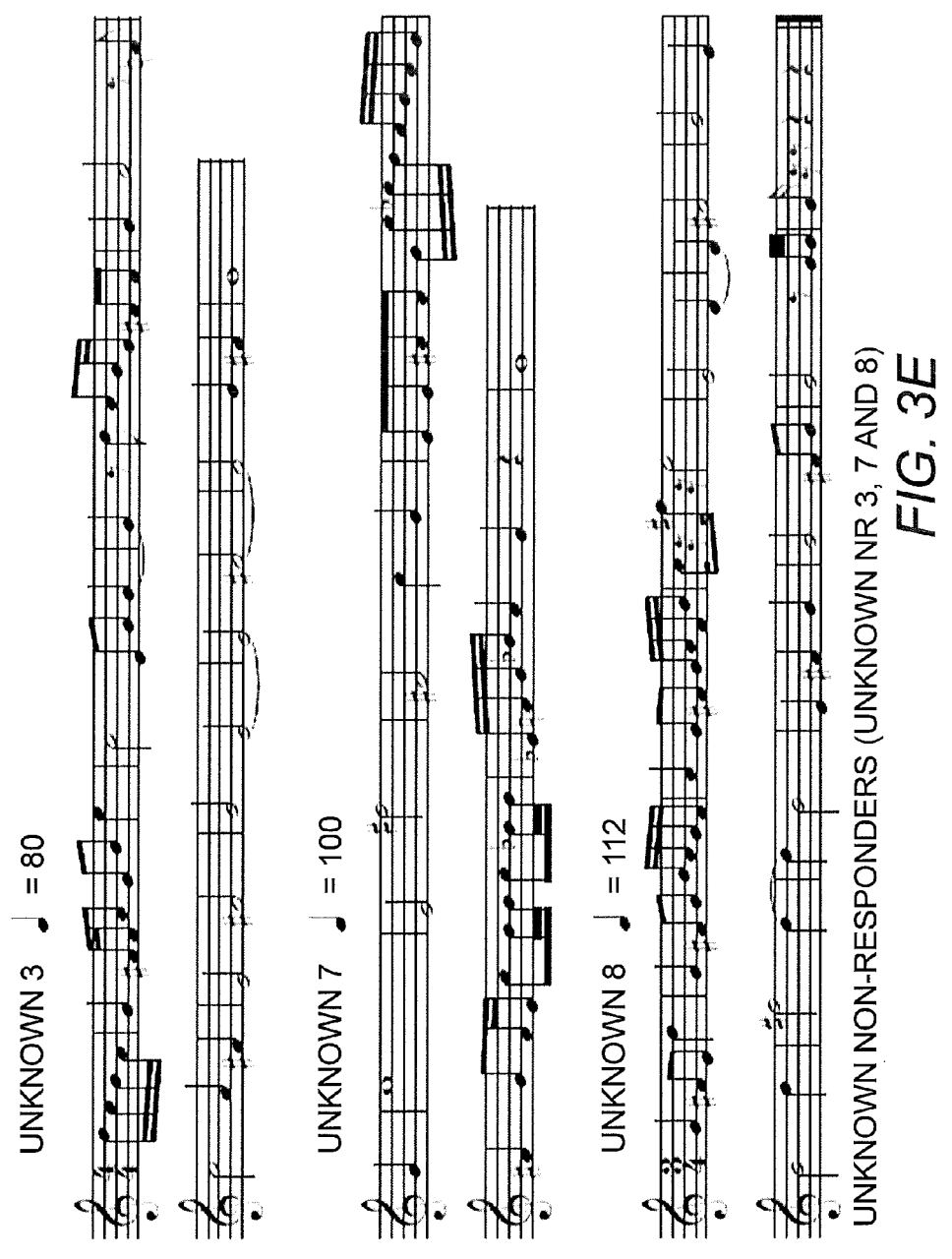
Figure 3F:
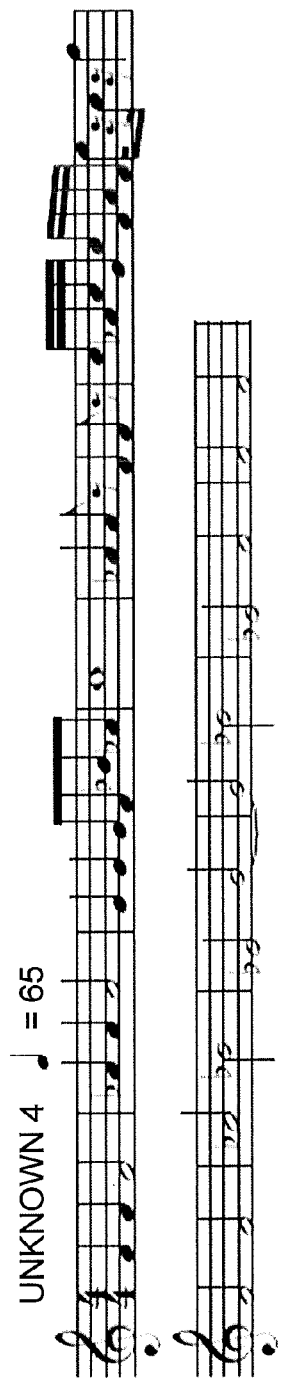
Figure 3F:
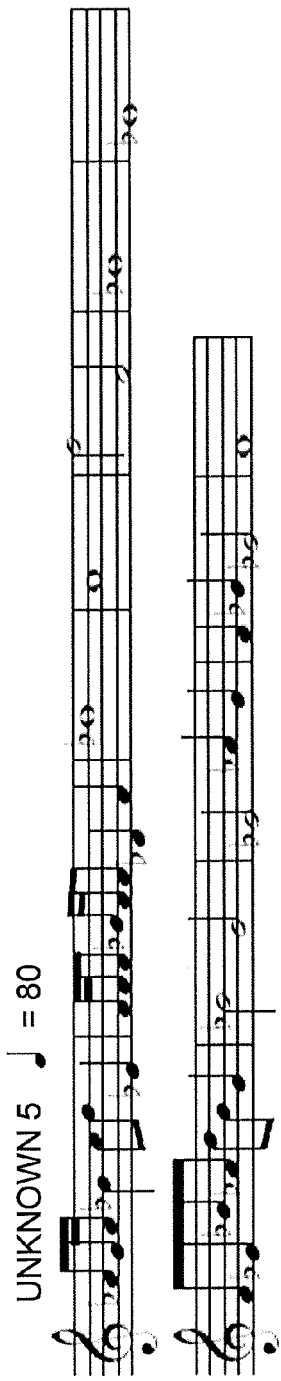
Figure 3F:
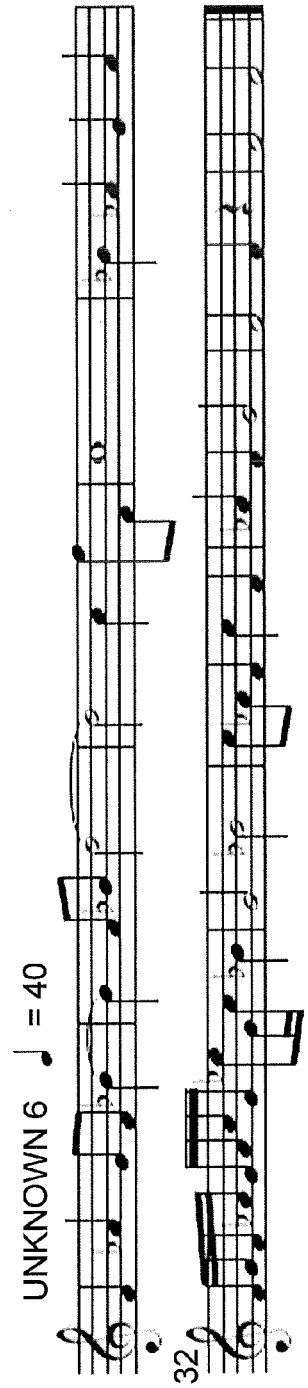
Figure 4A:
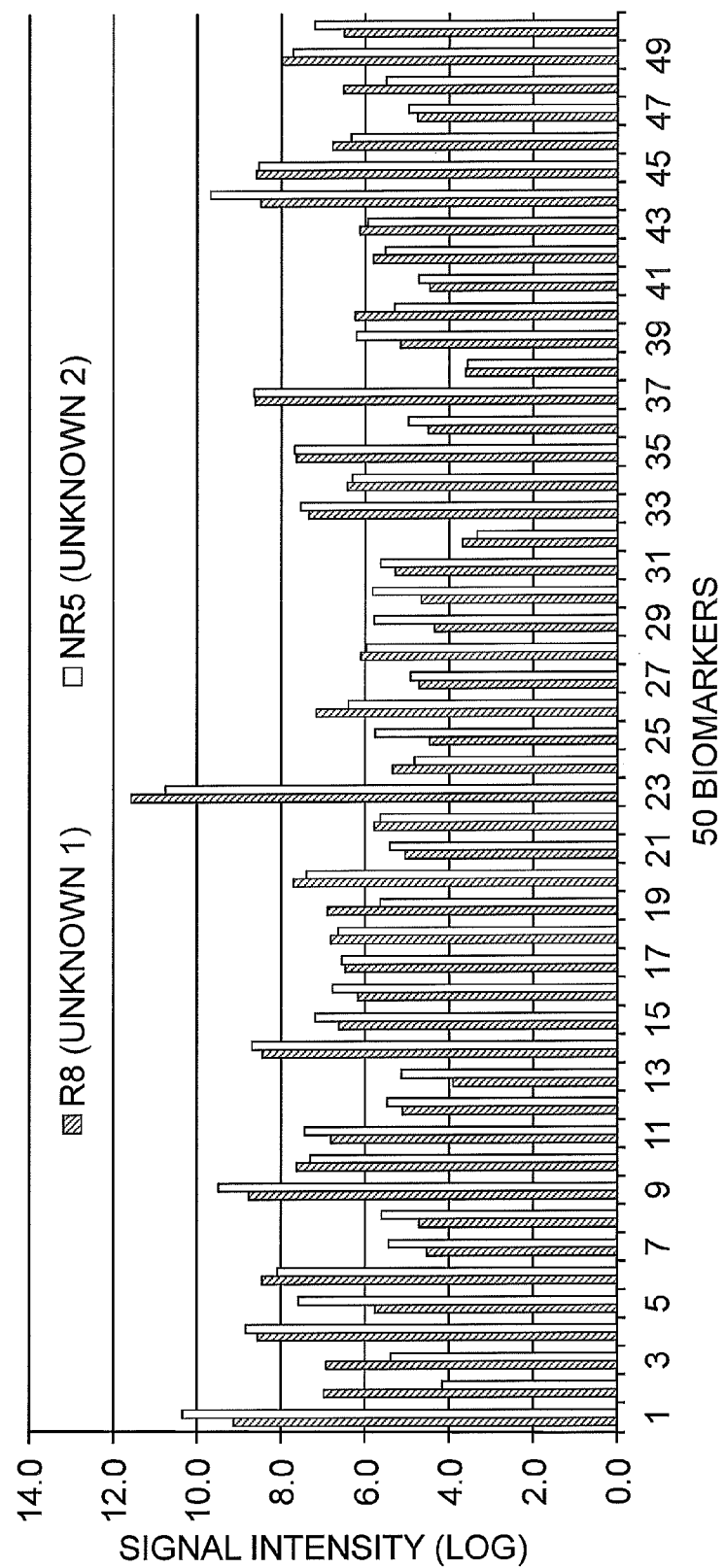
FIGS. 4A through 4G show class specific sound frequency pattern generation and recognition (SFPGR). Steps involved in sound frequency pattern generation and recognition are shown with sample data sets obtained from two unknown patients. Unknown 1 data were obtained from responder patient 8 and Unknown 2 data were obtained from non-responder patient 5.
Figure 4B:
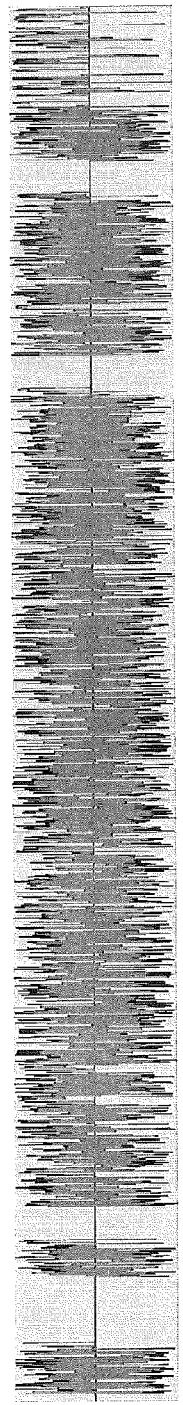
Figure 4C:
Figure 4D:
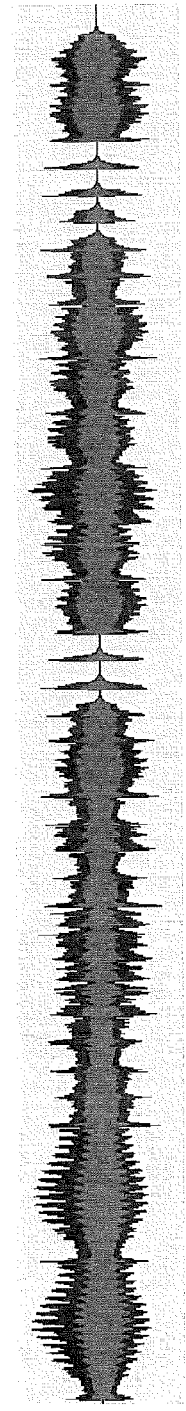
Figure 4E:
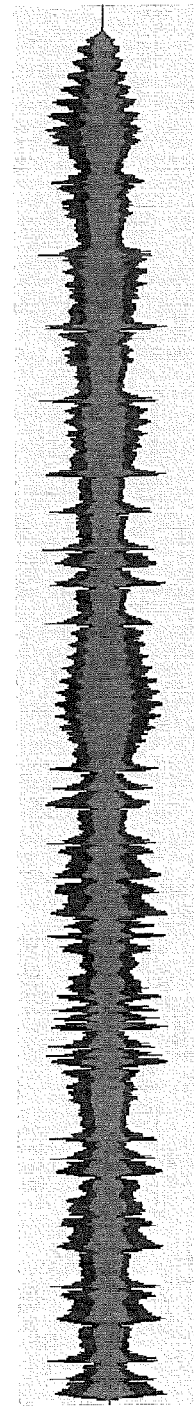
Figure 4F:
Figure 4G:
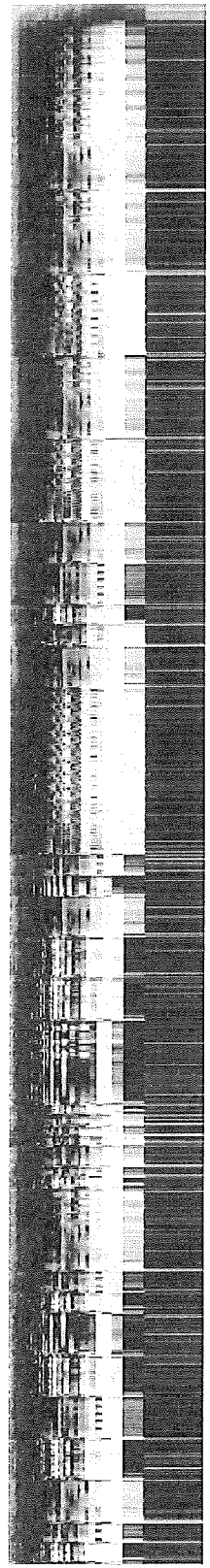
Figure 5:
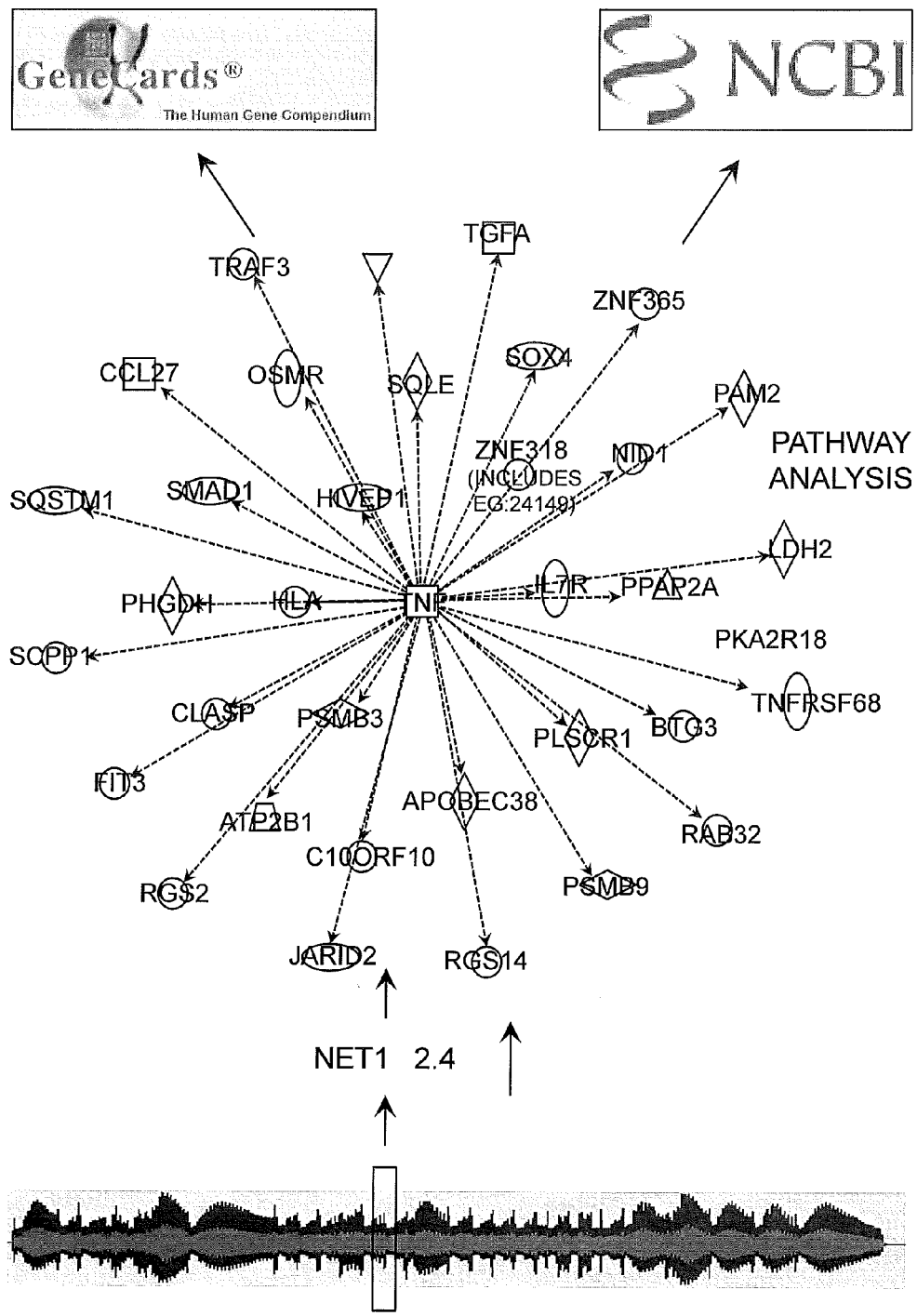
FIG. 5 is a schematic of a deconvolution program. As shown, the musical notes/sound frequencies can be readily converted to gene symbol/ID and intensity information and linked to public databases and/or pathway analysis tools.
Figure 6:
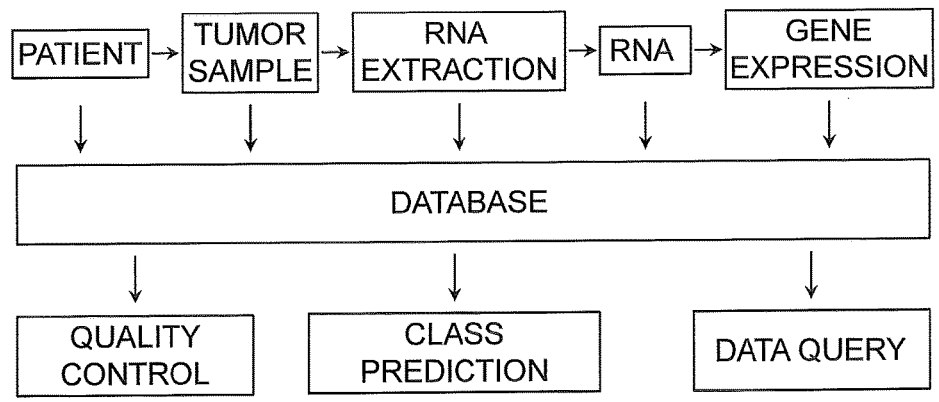
FIG. 6 shows an overview of an embodiment of a data base structure for the present invention. In this embodiment, the data base comprises deidentified patients' clinical information, tissue specification, sample (RNA/DNA) details, microarray data, composed tunes, reference SFPs, and known and unknown SFPs.
Figure 7A:
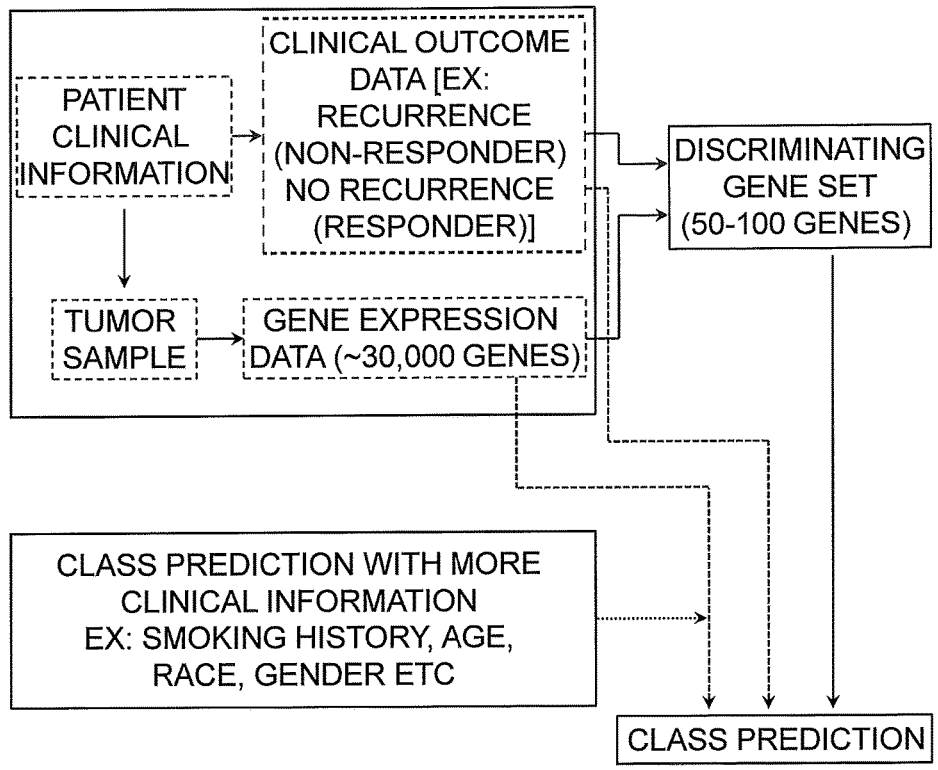
FIGS. 7A through 7C show class prediction and data integration capabilities of MMOA. Flow charts showing the steps involved in the MMOA to discriminate the major classes and sub-classes for personalized medicine applications are depicted in FIGS. 7A and 7B, respectively.
Figure 7B:
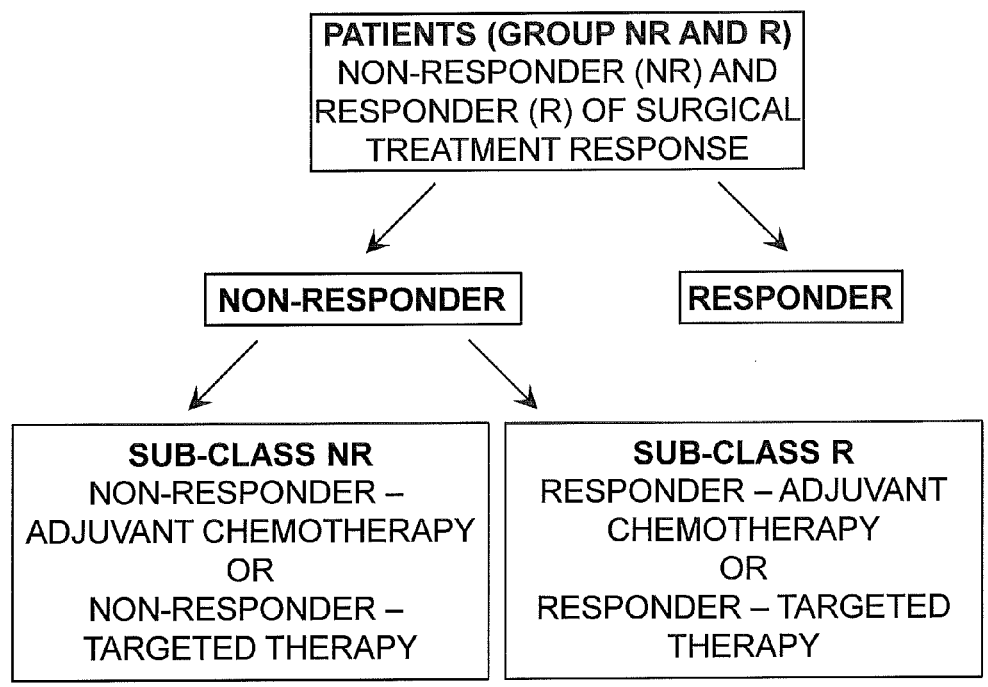
Figure 7C:
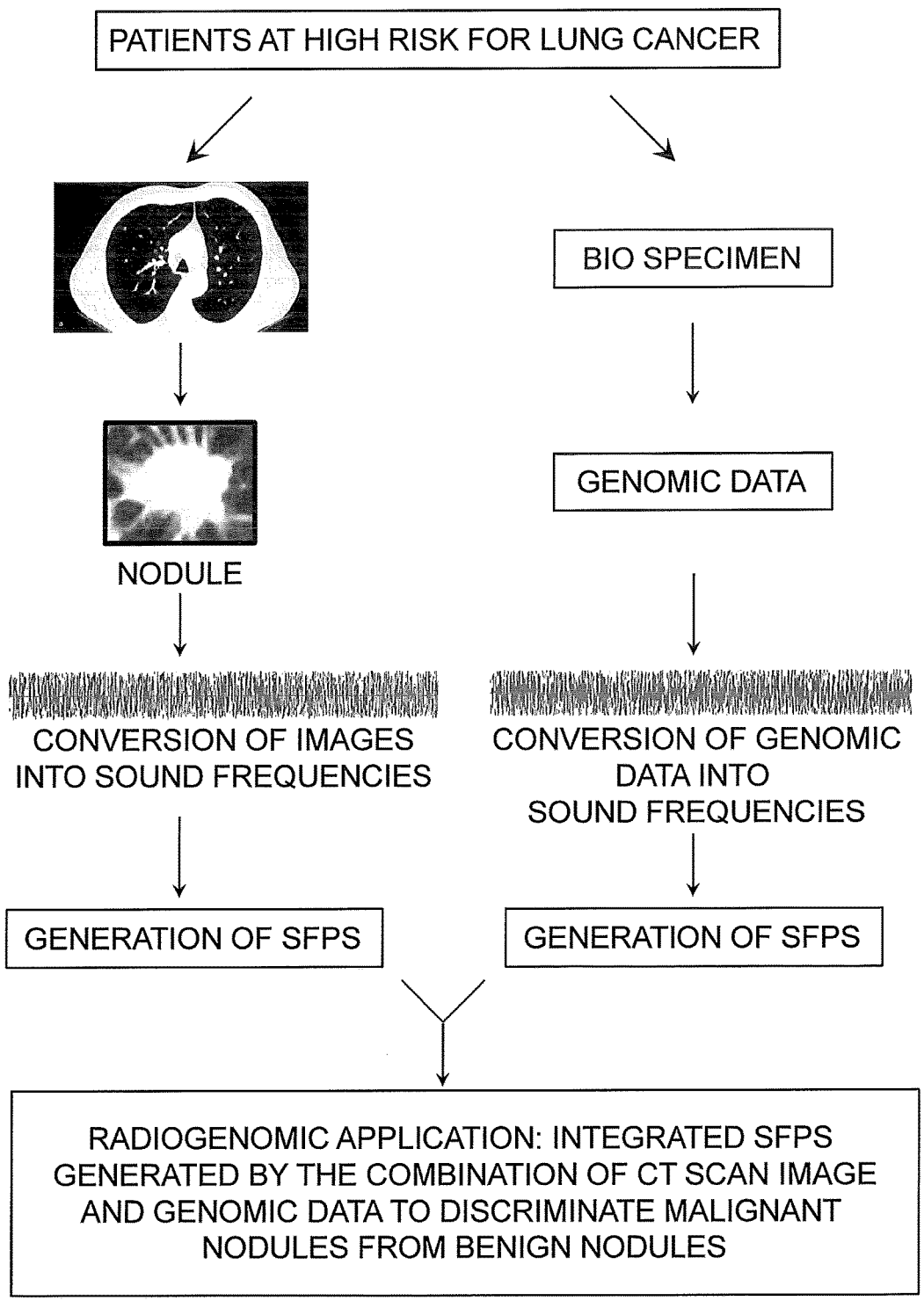
Figure 8:
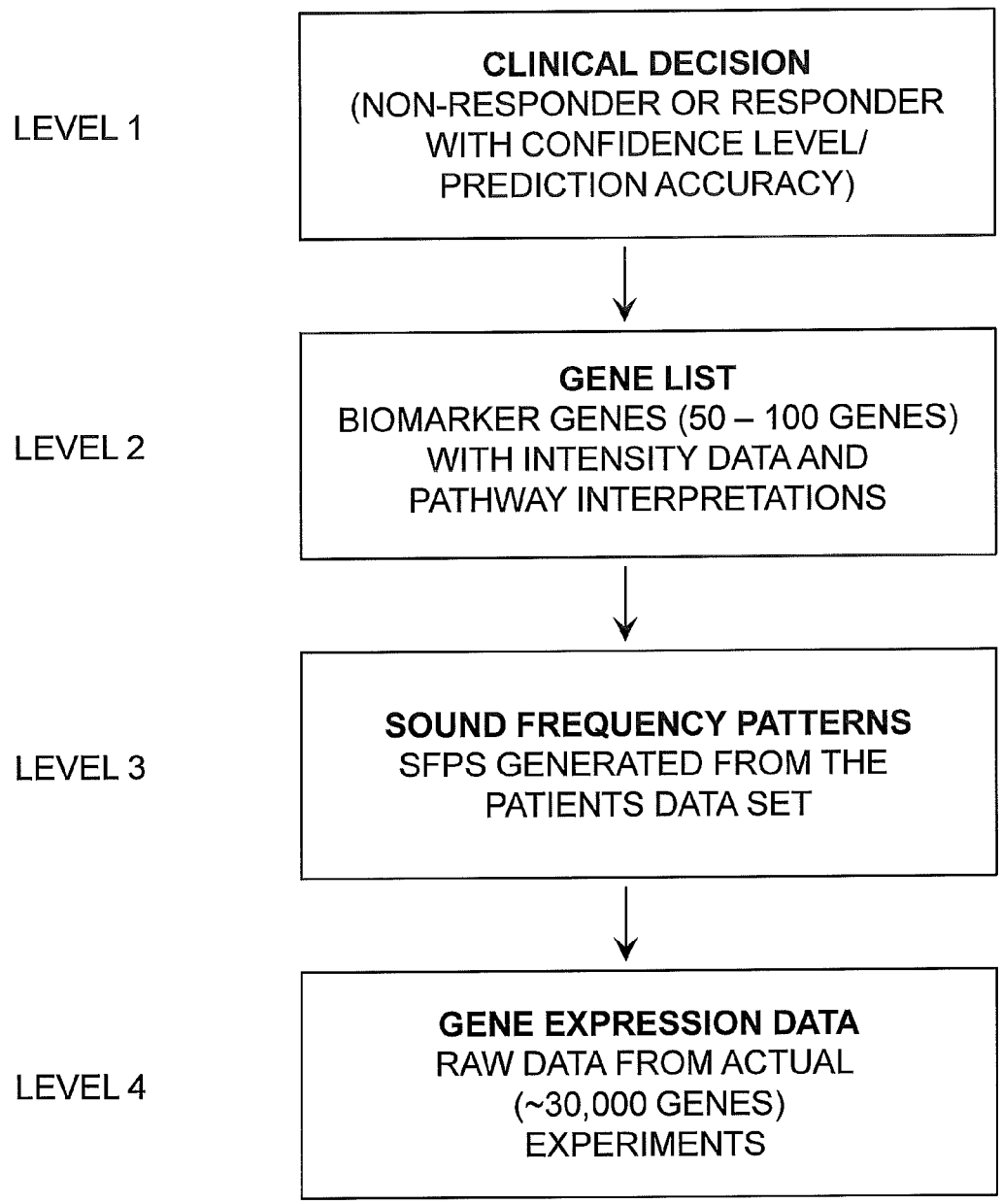
FIG. 8 provides an example of final data output from this method. As shown, clinical decision information can be obtained from a first level of the program. Gene list and the pathway information can be obtained from the next level. The details about SFPs are available in the third level. The raw data obtained from the entire gene expression/microarray data can be found in the last level.

A conversion rule was formulated to decipher the numbers (gene expression data/signal intensities) into musical notes/sound frequencies (see Table 1). After converting the numbers into pitches with rhythms, the notes were looked as a whole group. A pattern generation algorithm was created to generate sound frequency patterns (SFPs) ex: a string of eight notes from G to E or recurring notes ex: a lot of G or F. A key/tonal center i.e. G major and F minor respectively were selected to compose the music/generate SFPs. A coherent piece of music/SFP was composed/generated by observing and listening to the music. A reference/theme/framework tune or reference SFP was composed/generated using the NR and R mean values (see FIG. 3A). Known NR and R tunes/SFPs were composed/generated to fine tune the reference SFPs to train the model (FIGS. 3B and 3C). The tunes/SFPs were finalized by listening and observing to the composition/patterns, and fine tuned to match with the reference SFP/theme music by adjusting the location of the note or tempo etc. Microarray data from 8 patients were considered as the "unknown" test data set. A double blind test was performed to identify clinical outcome of 8 unknowns after fine tuned the model (FIGS. 3D-F). Steps involved in sound frequency pattern generation and recognition are shown with sample data set obtained from two unknown patients (unknown 1/responder patient 8 and unknown 2/non-responder patient 5) (see FIGS. 4A-4G). The tunes/SFPs are readily converted back to signal intensity and gene symbol/ID using a deconvolution program and can be linked to other public data bases (FIG. 5). A data base was created with reference and known SFPs and were compared with unknown SFPs for class prediction (see FIG. 6). The MMOA is a very versatile program and can handle more than one clinical parameter to classify a patient (see FIG. 7A). The application of MMOA to discriminate subclasses for personalized medicine is shown in FIG. 7B. In addition MMOA can be used to integrate data obtained from two or more technologies. An example of an integration approach for radiogenomic application is shown in FIG. 7C. Final data structure obtained from MMOA is shown in FIG. 8. Clinical decision (responder or non-responder) can be obtained from the first level. Gene list, signal intensity and pathway information can be obtained from the second level. The details about SFPs are available in the third level. The raw data obtained from all the genes can be found in the last level. The manually operated MMOA program was converted into cloud/web based computer program which was named Sound Frequency Pattern Generation and Recognition Algorithm (SFPGRA). The wire frames used for the SFPGRA are shown in FIGS. 9A-9L. Tables A through K below further describe the numbered elements and type as well as additional notations for the wireframes depicted in FIGS. 9A-9L.

TABLE A

Figure 9A:
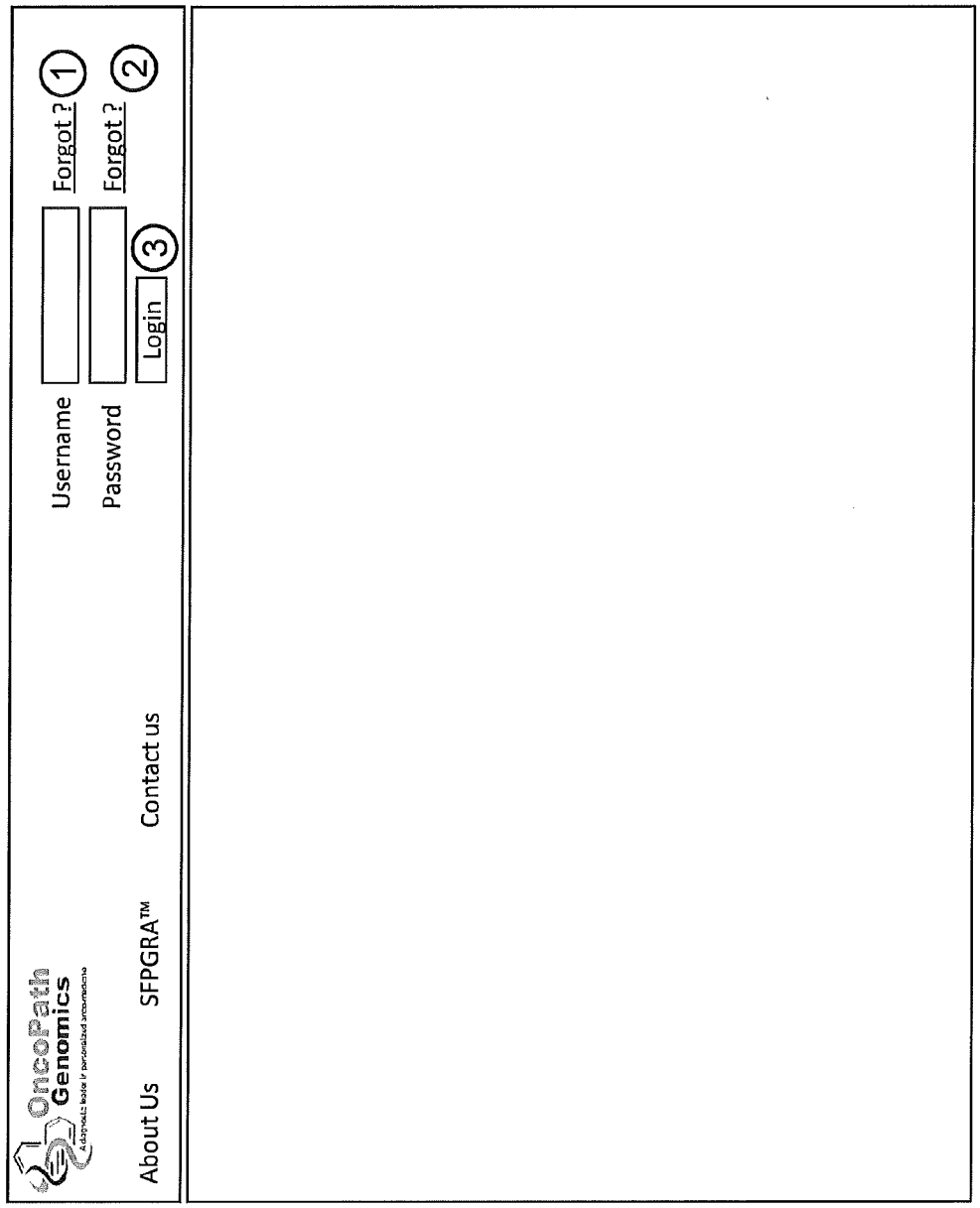

Corresponds to the Wireframe of FIG. 9A

| Title | | | Home |
|---|---|---|---|
| Version | | | 1.0 |
| Note: | | | |
| No. | Element | Type | Description |
| 1 | Forgot? | Link | Redirect the user to forgot username page |
| 2 | Forgot? | Link | Redirect the user to forgot password page |
| 3 | Login | Button | Authenticate the user's credentials |

TABLE B

Figure 9B:

Corresponds to the Wireframe of FIG. 9B

| Title | | | Home |
|---|---|---|---|
| Version | | | 1.0 |
| Note: | | | |
| No. | Element | Type | Description |
| 1 | Username | Text | From database |
| 2 | Secret question | Text | From database |
| 3 | Secret answer | Input box | User will enter the secret answer to their question. Secret question will be asked only when user logs in and the cookie dropped during the last visit is not found. |

TABLE C

Figure 9C:
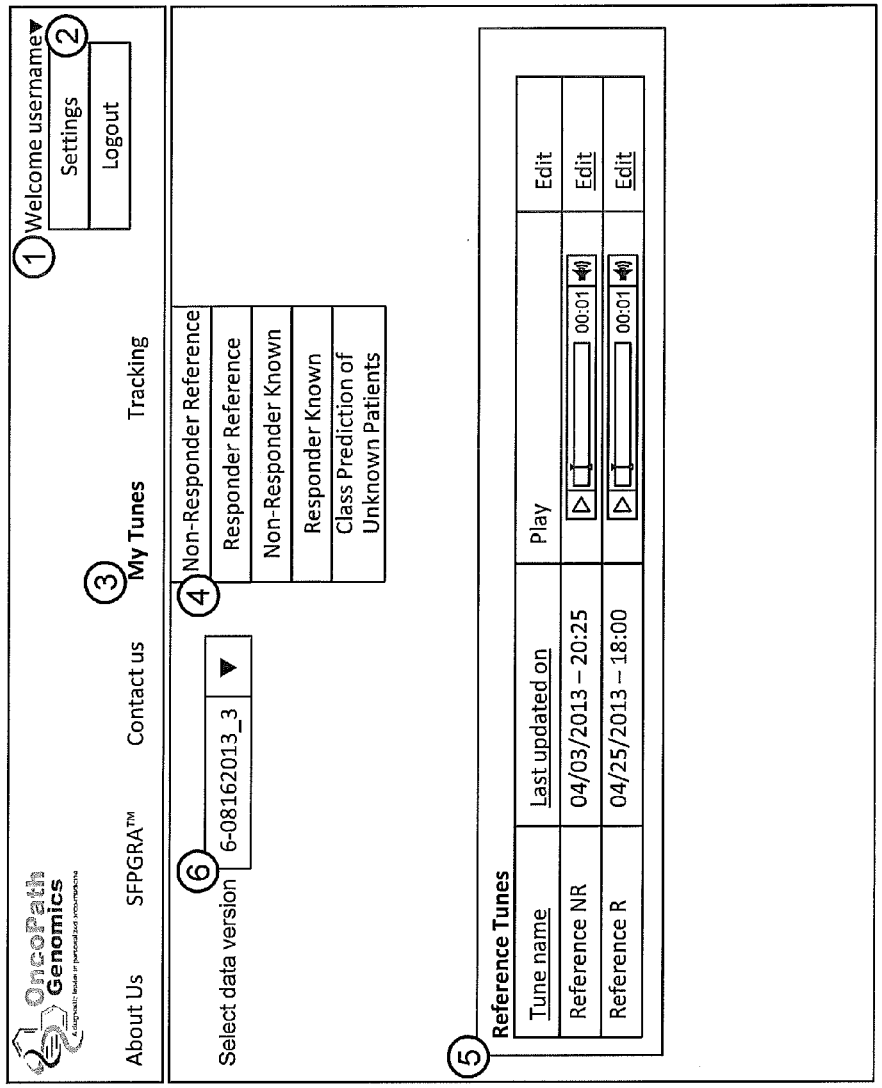

Corresponds to the Wireframe of FIG. 9C

| Title | | | Compose home page |
|---|---|---|---|
| Version | | | 1.0 |
| Note: This page is available to users with composer role. | | | |
| No. | Element | Type | Description |
| 1 | Welcome username | Text | Compose username will have an option of dropdown list |
| 2 | Dropdown list | Dropdown list | From Settings user can change username, password and email address |
| 3 | Link | Link | This is landing page for composer |
| 4 | Dropdown list | Dropdown list | On the rollover of My Tunes options list will come. |
| 5 | Data grid | Data grid | List of Reference tunes. |
| 6 | Select Data version | Dropdown list | This will list the version of data set uploaded A data set is a collection 3 files uploaded by the admin or site user. These three files are "mean NR and R", known NR and R" and "Unknowns" Changing the value from the list will load the data from selected data set. |

TABLE D

Figure 9D:
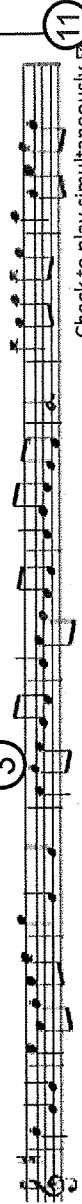

Corresponds to the Wireframe of FIG. 9D

| Title | | | Composer Reference Non-Responder OncoTune |
|---|---|---|---|
| Version | | | 1.0 |
| Note: Composer will compose the Reference Non-Responder OncoTune. The Reference Non-Responder OncoTune will be used in class prediction. | | | |
| No. | Element | Type | Description |
| 1 | Last updated | Text/ Date time | Date on which this version was last updated. This value gets updated when composer clicks Save this version button. |
| 2 | Comments | Text | Comments about tune |
| 3 | Mean NR notes | Staff | Notes generated from the Mean NR data uploaded. |

TABLE D-continued

Corresponds to the Wireframe of FIG. 9D

| | | | |
|---|---|---|---|
| | | | Using these notes composer will create reference NR tune. |
| 4 | Player | Music player | Play the notes from Mean NR notes |
| 5 | Reference NR OncoTune | Staff | On this staff composer will create new music by Double clicking to copy the note. Deleting notes from Tunes. |
| 6 | Copy all Notes from Mean NR to NR Tune | Button | Copy all notes from Mean NR to Ref NR OncoTune. |
| 7 | Clear NR Tune | Button | Clear Ref NR OncoTune staff |
| 8 | Bin | Image | Select a note and click bin delete it. |
| 9 | Save Changes | Button | Saves the Reference NR Tune |

TABLE E

Figure 9E:
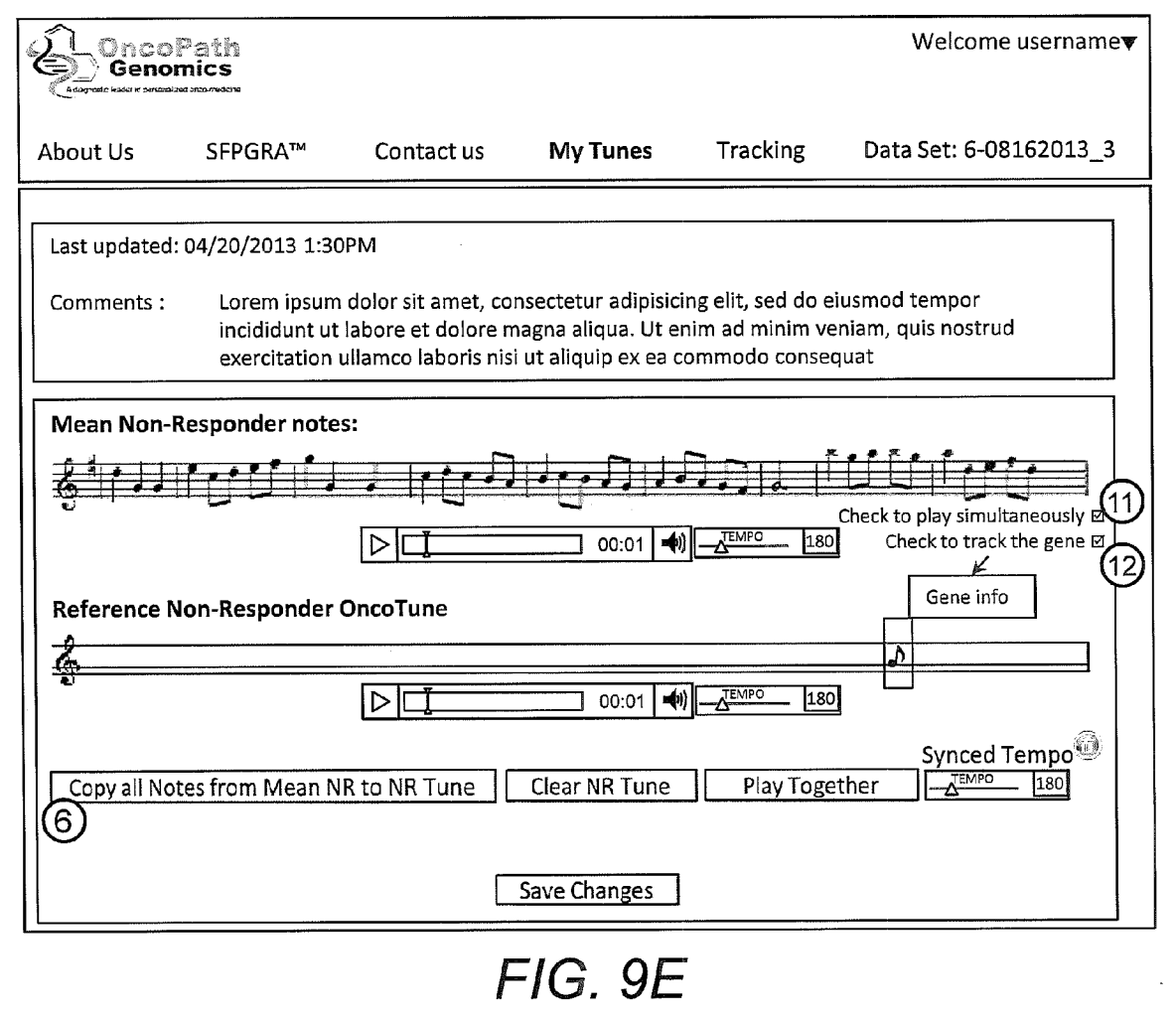

Corresponds to the Wireframe of FIG. 9E

| Title | | | Composer Reference Non-Responder OncoTune |
|---|---|---|---|
| Version | | | 1.0 |
| Note: | | | |

| No. | Element | Type | Description |
|---|---|---|---|
| 10 | Plays Together | Player | Plays all the tunes on the page |
| 11 | Check to apply composition rules | Checkbox | When checked the composition rules will be applied and notes will be highlighted. When unchecked composition rules will be removed and notes will come in normal/default colors. |
| 12 | Check to track the gene | Checkbox | When checked and composer rollovers mouse cursor on a notes it will show a popup at the mouse position with Gene information. When unchecked this feature will be turned off. |

TABLE F

Figure 9F:

Corresponds to the Wireframe of FIG. 9F

| Title | | | Composer Reference Responder OncoTune |
|---|---|---|---|
| Version | | | 1.0 |
| Note: Composer will compose the Reference Responder OncoTune. The Reference Responder OncoTune will be used in class prediction. | | | |

| No. | Element | Type | Description |
|---|---|---|---|
| 1 | Last updated | Text/ Date time | Date on which this version was last updated. This value gets updated when composer clicks Save this version button. |
| 2 | Comments | Text | Comments about tune |

TABLE F-continued

Corresponds to the Wireframe of FIG. 9F

| 3 | Mean R notes | Staff | Notes generated from the Mean R data uploaded. Using these notes composer will create reference R tune. |
|---|---|---|---|
| 4 | Player | Music player | Play the notes from Mean R notes |
| 5 | Reference R OncoTune | Staff | On this staff composer will create new music by Double clicking to copy the note. Deleting notes from Tunes. |
| 6 | Copy all Notes from Mean R to R Tune | Button | Copy all notes from Mean R to Ref R OncoTune. |
| 7 | Clear R Tune | Button | Clear Ref R OncoTune staff |
| 8 | Save Changes | Button | Saves the Reference R Tune |

TABLE G

Figure 9G:
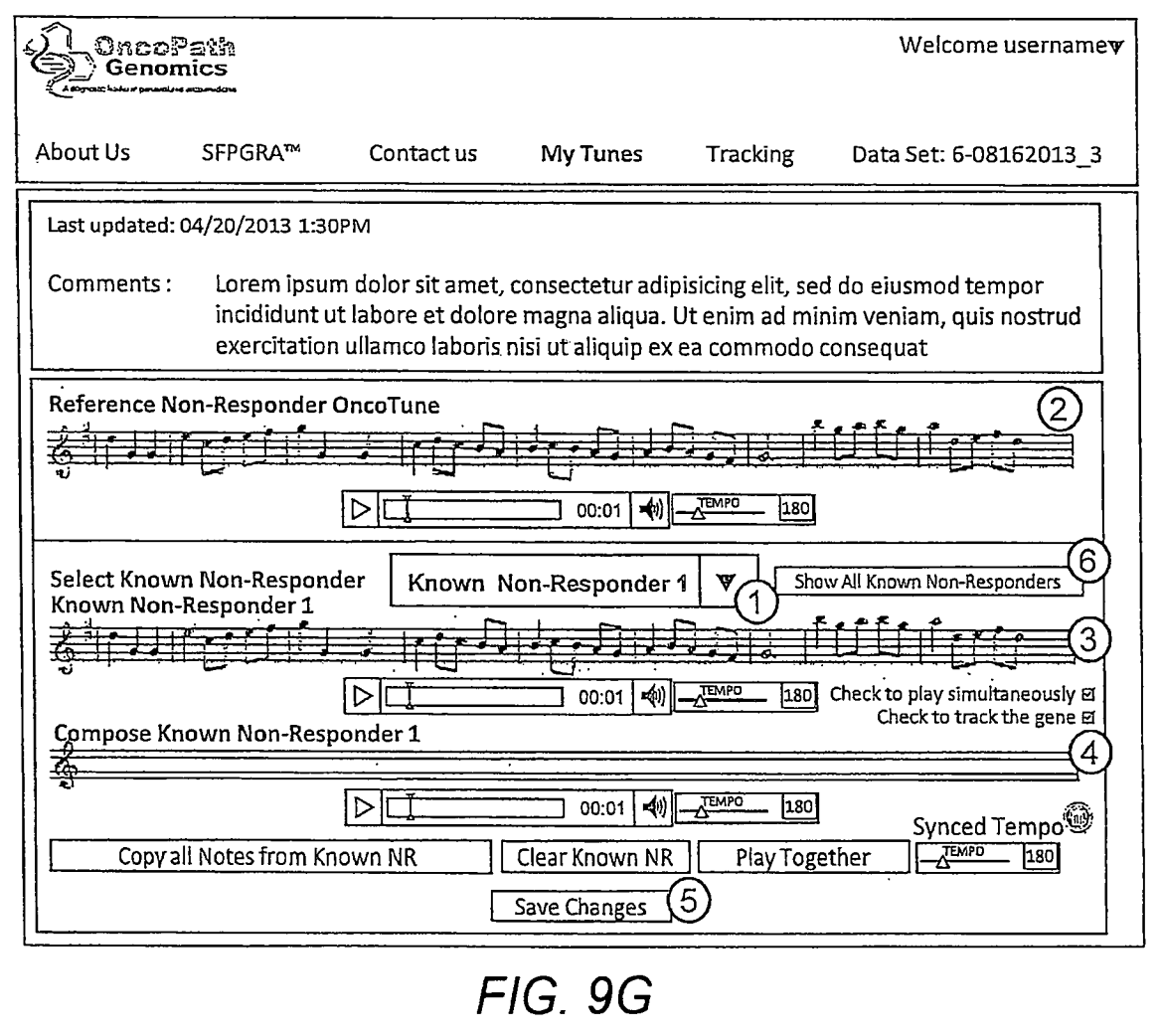

Corresponds to the Wireframe of FIG. 9G

| Title | | | Compose Known NR tune from NR Reference tune |
|---|---|---|---|
| Version | | | 1.0 |
| Note: | | | |
| On this page composer will compose known NR tunes from Reference Non-Responder OncoTune | | | |
| Composer can change either of the four tunes on this page. | | | |
| Composer can select known NR from the dropdown list 1 | | | |

| No. | Element | Type | Description |
|---|---|---|---|
| 1 | Known NR list | Dropdown list | List of all known NR. By default first items will be selected |
| 2 | Ref NR notes | Staff | Ref NR notes. This is read only. |
| 3 | Known NR | Staff | Known NR notes. These are for the known NR selected from the dropdown list 1 |
| 4 | Compose Known NR | Staff | Initially this will be blank. Composer will create a new tune from known NR here. |
| 5 | Save Changes | Button | Save changes |
| 6 | Show All Known Non-Responders | Button | Open or Pop up a new screen that will list all the Known Non-Responders |

TABLE H

Figure 9H:
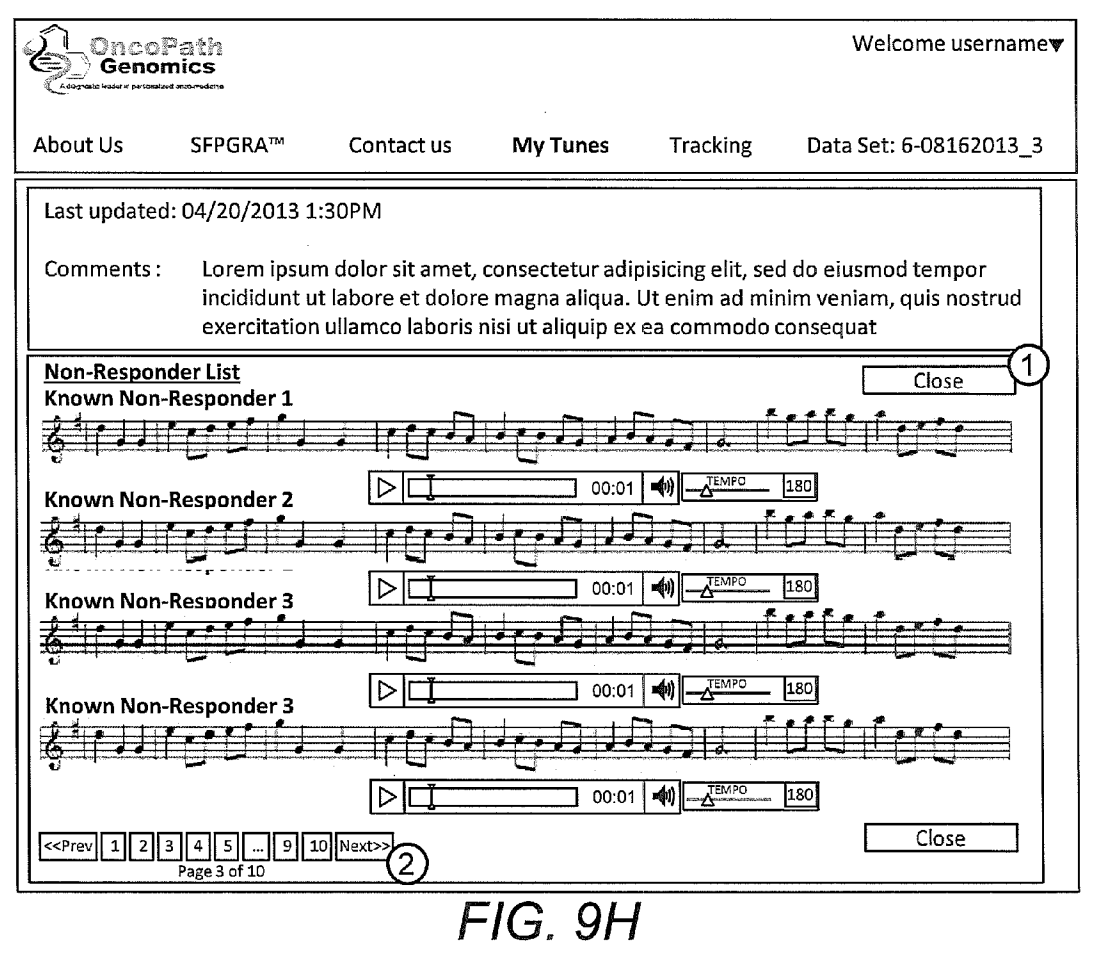

Corresponds to the Wireframe of FIG. 9H

| Title | | | Known NR or R list |
|---|---|---|---|
| Version | | | 1.0 |
| Note: | | | |

| No. | Element | Type | Description |
|---|---|---|---|
| 1 | Close | Button | This will take the user back to the previous screen, which are Know Non-Responder or Known Responder |

TABLE H-continued

Corresponds to the Wireframe of FIG. 9H

| | | | |
|---|---|---|---|
| 2 | Pagination | Pagination | Pagination will come only where there are more than 10 Known Non-Responders |

TABLE I

Figure 9I:
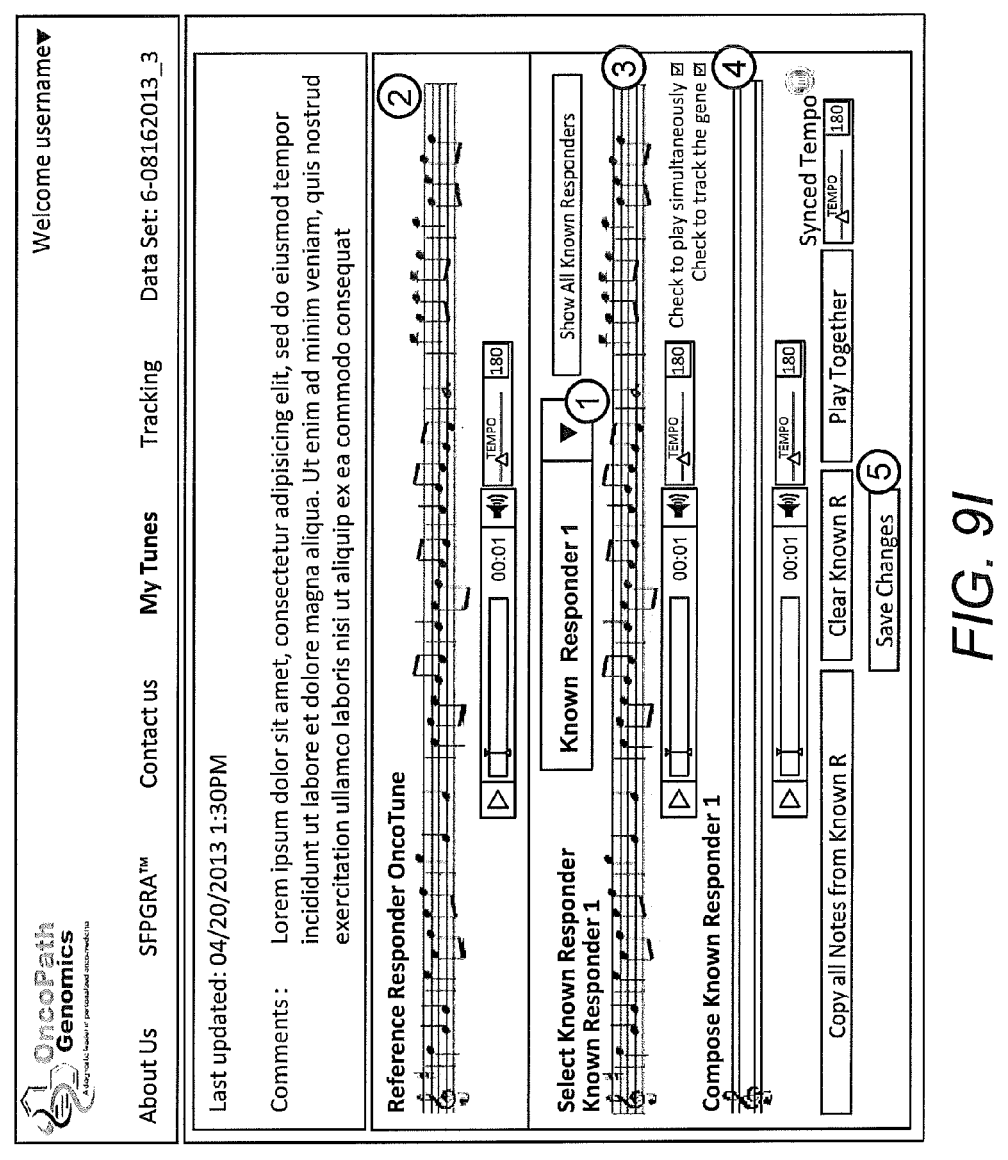

Corresponds to the Wireframe of FIG. 9I

| | |
|---|---|
| Title | Compose Known R tune from R Reference tune |
| Version | 1.0 |
| Note: | |

On this page composer will compose known R tunes from Reference Responder OncoTune
Composer can compose one known R tune at a time.
Composer can select known R from the dropdown list 1

| No. | Element | Type | Description |
|---|---|---|---|
| 1 | Known R list | Dropdown list | List of all known R. By default first items will be selected |
| 2 | Ref R notes | Staff | Ref R notes. This is read only. |
| 3 | Known R | Staff | Known R notes. These are for the known R selected from the dropdown list 1 |
| 4 | Compose Known R | Staff | Initially this will be blank. Composer will create a new tune from known R here. |
| 5 | Save Changes | Button | Save changes |

TABLE J

Figure 9J:
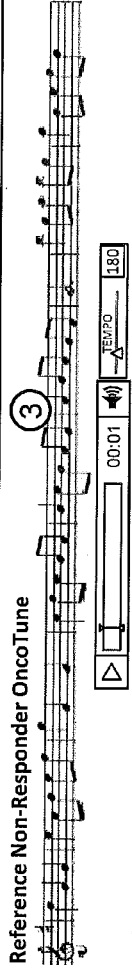
Figure 9K:
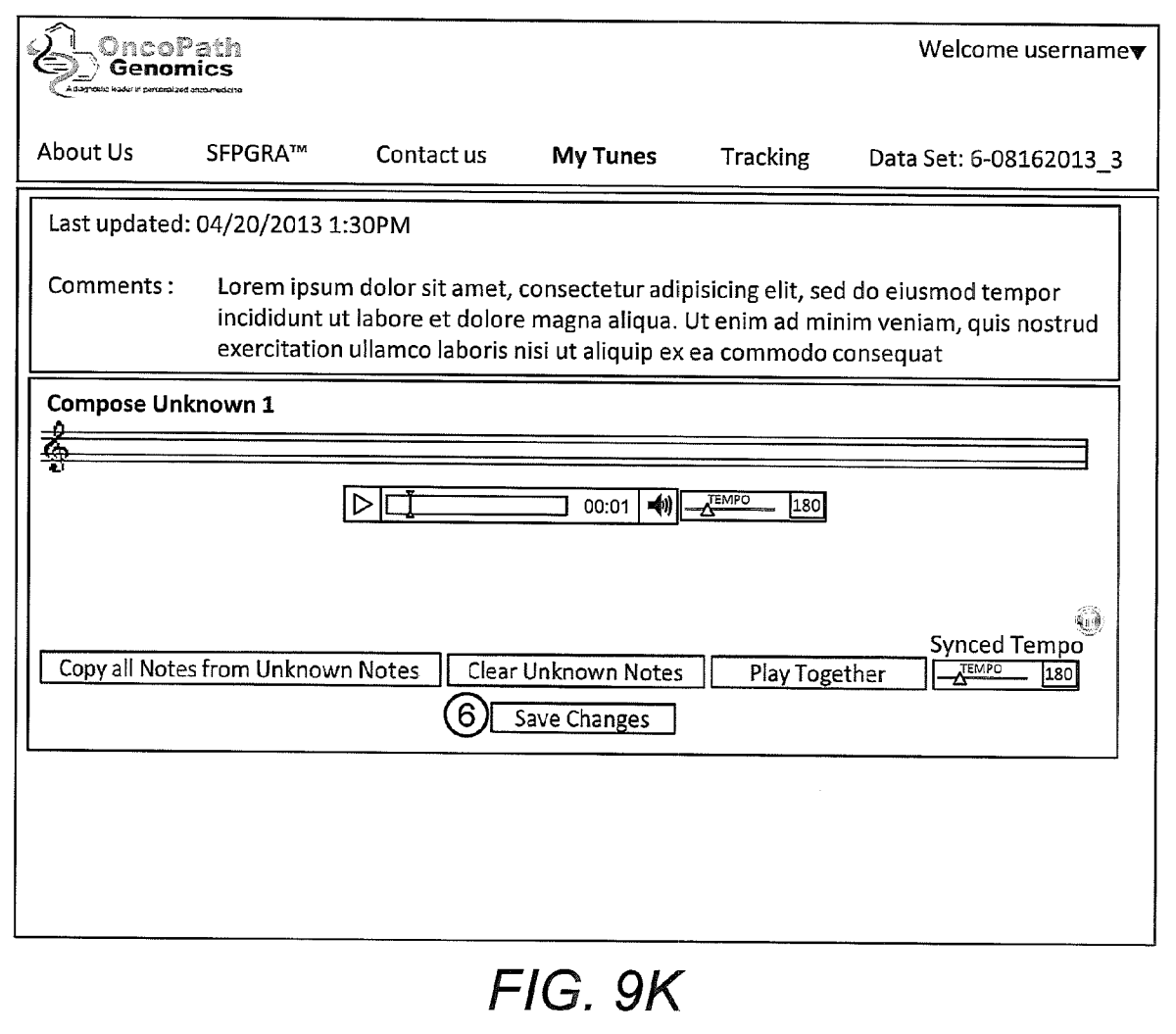

Corresponds to the Wireframes of FIG. 9J and 9K

| | |
|---|---|
| Title | Class prediction of Unknown patients |
| Version | 1.0 |
| Note: | |

On this page composer will predict the unknown patients based on Reference tunes.

| No. | Element | Type | Description |
|---|---|---|---|
| 1 | Unknowns | Dropdown list | List of all Unknown biomarkers Change the value will load that biomarkers in 5 |
| 2 | Result | Radio buttons | This will a three values Not know yet Non-Responder Responder |
| 3 | Reference Non-Responder | Staff | Reference Non-Responder tune |
| 4 | Reference Responder | Staff | Reference Responder tune |
| 5 | Unknown | Staff | Unknown notes that composer will compose to match either with Reference Non-Responder or Reference -Responder tunes |
| 6 | Save Changes | Button | Save changes |

TABLE K

Corresponds to the Wireframe of FIG. 9L

| | |
|---|---|
| Title | Tracking |
| Version | 1.0 |
| Note: | This page will track the changes made to the uploaded data |

| No. | Element | Type | Description |
|---|---|---|---|
| 1 | Tracking | Data grid | List the original biomarkers and changes made to them to create a tune |
| 2 | Select Unknown | Dropdown list | List of all the unknowns and All option to list all the unknowns |

Example 2: Methods

In step 1, a conversion rule was formulated to decipher the numbers (gene expression data) into musical notes/sound frequencies (see Table 1 below).

TABLE 1

The conversion rule used for the transfer of gene expression data (log 2 signal intensity) in to sound frequencies/musical notes.

| Intensity value (whole number) | Note | Intensity value (Decimal) | Rhythm |
|---|---|---|---|
| 1 | Tonic | 0 | Sixteenth |
| 2 | Supertonic | 1 | Sixteenth |
| 3 | Mediant | 2 | Sixteenth |
| 4 | Subdominant | 3 | Eight |
| 5 | Dominant | 4 | Eight |
| 6 | Sudmediant | 5 | Quarter |
| 7 | Leading Tone | 6 | Quarter |
| 8 | Tonic′ | 7 | Half |
| 9 | Supertonic′ | 8 | Half |
| 10 | Mediant′ | 9 | Whole |
| 11 | Subdominant′ | | |
| 12 | Dominant′ | | |

Other: Sharps (#) and Flats (b) as well as rests may be at Composer's discretion In step 2, after converting the numbers into pitches with rhythms, the notes were looked at as a whole group.

In step 3, a composition/pattern generation algorithm was created to generate SFPs with the notes/sound frequencies and the rules for composition as follows:
  a) Conversion vertical data into horizontal format.
  b) Search a set of data for any patterns (ex: 5.4, 6.4, 7.4, 6.4) that are apparent without changing the order of the set.
  c) Search for any outliers and mark them to not be used in composition.
  d) Figure out which number(s) occur most often and use that number/note as a tonic or a reciting tone.
  e) With the tonic note in mind, use any patterns discovered in #2 to create small sets of pitch orders (4-12 notes) with which to work with
  f) Use the pitch orders to create a motif or theme that can be used or repeated throughout the composing process
  g) Add rhythms and rests into the motif to make a more musical (sing-able) melody.
  h) If a common chord progress (IV-V-I) becomes apparent or is useful as a basis for the melody, it is a good option to use this when available.
  i) Always attempt to end a melody on a tonic or dominant
  j) Repeat steps a-i for each data set, being sure to relate all of the melodies to the main theme composed from the average data set.

A coherent piece of music/SFP was composed/generated by observing the SFPs and listening to the music.

In step 4, a reference/theme/framework music/SFP specific to each group (NR reference and R reference) was composed/generated using non-responders and responders mean values (see FIG. 3A), respectively.

In step 5, the theme/framework tune/SFP was used as the reference music/SFP to compose/generate the training sets (i.e. known non-responder and responder tunes/SFPs) to train the model (see FIGS. 3B and 3C).

In step 6, the tunes/SFPs were finalized by listening to the composition and observing the SFPs, and further refined to match with the reference/theme music/SFP by adjusting the location of the note or tempo, etc.

In step 7, data from 8 patients were considered as the test data set (i.e. unknowns). A double blind test was performed to identify clinical outcome of the unknowns after composing/generating the tune/SFP (see FIGS. 3D-3F). The clinical outcome was predicted correctly by observing the SFPs and listening to the musical notes. 100% prediction accuracy was achieved using the current model of the present invention.

In step 8, initially the entire gene expression data were converted into musical notes using excel program and with the help of a music composer. Manual MMOA took a longer time for class prediction. The manually operated MMOA program was converted into cloud/web based software (SF-PGRA). The program can be operated using any of the following programs. The wire frames used for the SFPGRA are listed in FIGS. 9A through 9L and their numbered elements and type as well as additional notations for the wireframes depicted in FIGS. 9A-9L are provide in Tables A through K above.

| | | |
|---|---|---|
| @ | Microsoft Internet Explorer | 7.x+ |
| @ | Mozilla Firefox | 9.x+ |
| @ | Google Chrome | 16.x+ |
| @ | Apple Safari | 5.x+ |

Audio Files

The tunes/SFPs can be listened to by playing any musical instrument mode using any musical software. For these tests, the audios (midi files) were recorded in violin and piano playing mode. Two tunes/SFPs (NR reference and R ref) were composed as the reference/theme tunes/SFPs. Three NR tunes/SFPs and three R tunes/SFPs were composed/generated as the training set. Eight tunes (4NR and 4R) were composed/generated to test and validate the model.

Deconvolution of Musical Notes/Sound Frequencies to Signal Intensity and Gene Symbol/ID The tunes/SFPs are readily converted back to signal intensity and gene symbol/ID using a deconvolution program. It can be linked to pathway analysis tools and public data bases. The schematic detail of the deconvolution program is shown in FIG. 5.

Example 3: Results

Conventional Microarray Data Analysis

The microarray data was normalized using Robust Multiarray Average (RMA) procedure on Affymetrix GeneChip Operating Software (GCOS). For further analysis, the data was filtered and the probes that do not change were removed from the analysis. The data was further analyzed in R statistical language using standard Bioconductor packages and custom written codes. The top 50 biomarkers and their signal intensities used for class prediction are shown in Table 2.

Classifier built on the training dataset was applied to predict the clinical outcome of the 8 unknown patients (unknown test data set). The results are show in Table 3. To determine prediction accuracy, sample and data permutations were performed. Each sample was removed, and about 80% percent of genes were randomly sampled 1000 times from the filtered data-set. Each time the classifier learning procedure was repeated and then applied to unknown patients to predict the outcome. Prediction accuracies for 7 unknown patients are very high, around or higher than 95% (with about 2-3% confidence interval). The sample unknown 4 predicted as non-respondent with confidence accuracy within 61%-72%. The prediction accuracy was later compared with the original clinical outcome of the patients (Table 3). The prediction accuracy was found to be 62.5%. Three samples (marked *) out 8 samples were predicted incorrectly.

TABLE 2

Top 50 biomarkers differentially expressed in responders and non-responders of surgical treatment. NR mean: Non-responders mean (n = 23); R mean: Responders mean (n = 13); NR and R means were used to composed/generate reference tunes/reference SFPs. KNR1, KNR2 and KNR4: Known non-responders testing set. KR3, KR6 and KR7: Known responders testing set. UN1/R8: Unknown 1/Responder 8; UN2/NR5: Unknown 2/Nonresponder 5. Data for other 6 unknowns (3 NR and 3 R) samples are not shown.

| Affy_Probe ID | NR Mean | R Mean | KNR1 | KNR2 | KNR4 | KR3 | KR6 | KR7 | UN1/R8 | UN2/NR5 |
|---|---|---|---|---|---|---|---|---|---|---|
| 201830_s_at | 10.07 | 9.69 | 7.78 | 8.83 | 9.97 | 8.95 | 6.83 | 7.78 | 9.12 | 10.33 |
| 215078_at | 3.91 | 4.25 | 5.14 | 3.80 | 3.99 | 8.05 | 8.10 | 8.74 | 6.98 | 4.17 |
| 241272_at | 4.13 | 4.36 | 4.33 | 4.00 | 4.19 | 4.06 | 7.14 | 8.04 | 6.91 | 5.39 |
| 200656_s_at | 10.91 | 10.70 | 10.97 | 11.14 | 10.01 | 10.95 | 8.77 | 8.68 | 8.56 | 8.83 |
| 213915_at | 6.41 | 6.61 | 6.12 | 7.01 | 7.02 | 8.63 | 10.86 | 7.45 | 5.77 | 7.59 |
| 243256_at | 6.50 | 6.70 | 6.72 | 6.87 | 7.18 | 7.28 | 9.25 | 8.60 | 8.45 | 8.09 |
| 243819_at | 3.78 | 3.98 | 3.75 | 4.00 | 4.51 | 4.07 | 6.62 | 5.10 | 4.53 | 5.45 |
| 240265_at | 3.43 | 3.62 | 3.51 | 3.63 | 4.26 | 3.08 | 6.38 | 5.62 | 4.72 | 5.62 |
| 232311_at | 5.48 | 5.67 | 5.90 | 5.62 | 6.05 | 6.17 | 10.18 | 9.52 | 8.77 | 9.49 |
| 236725_at | 5.61 | 5.80 | 5.48 | 5.51 | 5.56 | 6.59 | 9.00 | 7.77 | 7.62 | 7.29 |
| 211794_at | 5.82 | 6.00 | 6.40 | 6.20 | 6.03 | 6.58 | 8.99 | 8.33 | 6.81 | 7.43 |
| 244777_at | 5.25 | 5.43 | 5.22 | 5.37 | 5.90 | 5.58 | 7.72 | 6.44 | 5.11 | 5.49 |
| 238575_at | 4.16 | 4.35 | 3.75 | 4.08 | 4.10 | 3.68 | 8.81 | 4.67 | 3.92 | 5.14 |
| 204103_at | 7.83 | 7.99 | 7.25 | 7.93 | 8.62 | 9.82 | 11.78 | 9.70 | 8.43 | 8.69 |
| 242946_at | 5.35 | 5.51 | 5.53 | 5.55 | 6.56 | 5.75 | 8.60 | 7.71 | 6.63 | 7.19 |
| 224582_s_at | 9.04 | 8.88 | 8.66 | 8.61 | 8.88 | 8.94 | 5.57 | 5.60 | 6.17 | 6.77 |

TABLE 2-continued

Top 50 biomarkers differentially expressed in responders and non-responders of surgical treatment. NR mean: Non-responders mean (n = 23); R mean: Responders mean (n = 13); NR and R means were used to composed/generate reference tunes/reference SFPs. KNR1, KNR2 and KNR4: Known non-responders testing set. KR3, KR6 and KR7: Known responders testing set. UN1/R8: Unknown 1/Responder 8; UN2/NR5: Unknown 2/Non-responder 5. Data for other 6 unknowns (3 NR and 3 R) samples are not shown.

| Affy_Probe ID | NR Mean | R Mean | KNR1 | KNR2 | KNR4 | KR3 | KR6 | KR7 | UN1/R8 | UN2/NR5 |
|---|---|---|---|---|---|---|---|---|---|---|
| 230110_at | 5.50 | 5.66 | 5.29 | 5.93 | 6.31 | 5.94 | 8.73 | 6.91 | 6.47 | 6.55 |
| 238063_at | 5.82 | 5.97 | 6.31 | 6.04 | 5.95 | 6.01 | 8.42 | 7.91 | 6.82 | 6.64 |
| 236495_at | 3.87 | 4.02 | 4.58 | 3.73 | 3.68 | 4.80 | 7.88 | 8.82 | 6.90 | 5.64 |
| 230006_s_at | 7.87 | 7.73 | 7.40 | 7.82 | 7.58 | 8.38 | 5.23 | 5.68 | 7.70 | 7.40 |
| 227182_at | 5.48 | 5.62 | 5.10 | 5.50 | 5.87 | 5.23 | 7.59 | 5.59 | 5.05 | 5.42 |
| 240260_at | 4.86 | 5.00 | 4.62 | 5.22 | 5.38 | 4.73 | 7.12 | 7.19 | 5.79 | 5.65 |
| 201417_at | 11.61 | 11.48 | 11.26 | 11.40 | 11.78 | 11.25 | 8.22 | 10.48 | 11.57 | 10.75 |
| 240652_at | 3.97 | 4.10 | 3.76 | 4.05 | 4.30 | 4.21 | 6.17 | 6.07 | 5.35 | 4.83 |
| 1559037_a_at | 4.05 | 4.18 | 4.27 | 4.19 | 4.52 | 3.73 | 6.11 | 6.37 | 4.48 | 5.76 |
| 206296_x_at | 5.52 | 5.65 | 5.39 | 5.86 | 5.73 | 5.44 | 7.68 | 6.63 | 7.17 | 6.40 |
| 239205_s_at | 4.37 | 4.50 | 5.10 | 5.26 | 4.32 | 5.76 | 9.04 | 6.82 | 4.72 | 4.93 |
| 233204_at | 4.74 | 4.87 | 5.02 | 4.69 | 4.50 | 4.74 | 6.89 | 6.54 | 6.11 | 5.98 |
| 210549_s_at | 4.49 | 4.62 | 4.67 | 4.45 | 5.45 | 4.71 | 8.77 | 5.25 | 4.36 | 5.79 |
| 1569369_at | 4.02 | 4.14 | 3.83 | 4.43 | 3.64 | 6.06 | 7.20 | 5.60 | 4.67 | 5.83 |
| 1557797_a_at | 4.05 | 4.17 | 3.78 | 4.61 | 5.11 | 3.88 | 6.56 | 5.78 | 5.30 | 5.64 |
| 1557578_at | 2.92 | 3.05 | 2.80 | 2.56 | 3.40 | 3.12 | 6.31 | 6.04 | 3.69 | 3.33 |
| 213958_at | 7.14 | 7.26 | 7.07 | 7.41 | 7.57 | 7.25 | 8.45 | 7.51 | 7.34 | 7.54 |
| 244357_at | 4.28 | 4.40 | 4.31 | 4.43 | 4.37 | 4.10 | 7.37 | 6.75 | 6.43 | 6.31 |
| 227677_at | 6.80 | 6.91 | 6.56 | 7.07 | 7.08 | 6.98 | 9.26 | 8.32 | 7.63 | 7.68 |
| 214369_s_at | 4.25 | 4.37 | 4.79 | 4.68 | 4.69 | 4.04 | 6.03 | 5.50 | 4.52 | 4.98 |
| 204485_s_at | 9.27 | 9.16 | 9.77 | 9.36 | 8.57 | 9.44 | 6.60 | 7.03 | 8.62 | 8.64 |
| 234640_x_at | 3.43 | 3.54 | 4.09 | 3.45 | 3.69 | 3.84 | 4.80 | 6.02 | 3.62 | 3.57 |
| 236301_at | 5.19 | 5.31 | 4.67 | 5.39 | 5.73 | 5.73 | 8.06 | 5.88 | 5.17 | 6.21 |
| 241505_at | 4.53 | 4.64 | 4.19 | 4.61 | 5.26 | 4.53 | 6.38 | 6.25 | 6.26 | 5.31 |
| 1556472_s_at | 4.11 | 4.22 | 3.84 | 4.26 | 4.25 | 4.02 | 6.58 | 4.66 | 4.47 | 4.73 |
| 1560706_at | 4.70 | 4.81 | 4.70 | 4.49 | 5.32 | 5.25 | 6.84 | 5.56 | 5.81 | 5.53 |
| 235040_at | 6.38 | 6.27 | 6.62 | 6.30 | 5.75 | 6.19 | 5.03 | 5.60 | 6.13 | 5.94 |
| 201428_at | 8.83 | 8.72 | 6.94 | 8.50 | 8.99 | 6.81 | 4.74 | 7.06 | 8.48 | 9.67 |
| 224676_at | 9.53 | 9.42 | 9.86 | 9.13 | 9.48 | 8.87 | 7.96 | 7.91 | 8.59 | 8.54 |
| 214219_x_at | 5.51 | 5.61 | 5.37 | 5.74 | 5.91 | 5.35 | 7.45 | 6.55 | 6.78 | 6.33 |
| 1555259_at | 4.13 | 4.23 | 4.03 | 3.98 | 3.83 | 5.29 | 8.39 | 4.95 | 4.77 | 4.97 |
| 210988_s_at | 7.29 | 7.18 | 7.22 | 7.40 | 6.58 | 7.48 | 4.74 | 5.25 | 6.52 | 5.51 |
| 210225_x_at | 7.74 | 7.84 | 7.87 | 7.89 | 8.03 | 8.33 | 9.00 | 8.80 | 7.98 | 7.72 |
| 206804_at | 5.45 | 5.55 | 5.48 | 5.61 | 5.68 | 5.88 | 9.80 | 6.93 | 6.50 | 7.20 |

TABLE 3

Prediction accuracy of conventional data analysis method was calculated by comparing the predicted outcomes with the original clinical outcome.

| S. No | Status | Clinical outcome | Predicted with Bio-Conductor |
|---|---|---|---|
| 1 | Unknown 1 | Responder | Non-Responder* |
| 2 | Unknown 2 | Non-Responder | Non-Responder |
| 3 | Unknown 3 | Non-Responder | Non-Responder |
| 4 | Unknown 4 | Responder | Non-Responder* |
| 5 | Unknown 5 | Responder | Responder |
| 6 | Unknown 6 | Responder | Responder |
| 7 | Unknown 7 | Non-Responder | Responder* |
| 8 | Unknown 8 | Non-Responder | Non-Responder |

*Three samples out 8 were predicted incorrectly

Prediction accuracy of MMOA is shown in Table 4. Eight tunes/SFPs were composed to validate the algorithm and they were predicted with 100% accuracy in double blind studies.

TABLE 4

Comparison of prediction accuracy of conventional microarray analysis method with MMOA.

| S. No | Status | Clinical outcome | Predicted with Bio-Conductor | Predicted with MMOA |
|---|---|---|---|---|
| 1 | Unknown 1 | Responder | Non-Responder | Responder |
| 2 | Unknown 2 | Non-Responder | Non-Responder | Non-Responder |
| 3 | Unknown 3 | Non-Responder | Non-Responder | Non-Responder |
| 4 | Unknown 4 | Responder | Non-Responder | Responder |
| 5 | Unknown 5 | Responder | Responder | Responder |
| 6 | Unknown 6 | Responder | Responder | Responder |
| 7 | Unknown 7 | Non-Responder | Responder | Non-Responder |
| 8 | Unknown 8 | Non-Responder | Non-Responder | Non-Responder |

What is claimed is:

1. A method of classifying a patient suffering from a disease as a responder or a non-responder to a selected treatment for the disease, said method comprising analyzing a sample from the patient for signal intensities of RNA, DNA or protein in the sample using an RNA, DNA or protein microarray;

filtering a data set of the signal intensities generated from the microarray and converting the signal intensities to musical notes, sound frequencies, class specific tunes and/or sound frequency patterns;

assigning an audio tune and/or sound frequency pattern capturing the filtered data to the patient by listening and/or observing the class specific tunes and/or sound frequency patterns; and classifying the patient as a responder or a non-responder by comparing their audio tune and/or sound frequency pattern to an audio tune and/or sound frequency pattern previously identified for known responders or known non-responders.

2. The method of claim 1 wherein the patient is suffering from cancer.

3. The method of claim 1 wherein the patient is suffering from lung cancer.

4. The method of claim 1 wherein the audio tune capturing the filtered data from the microarray is assigned manually using a mathematical musical orchestral algorithm.

5. The method of claim 1 wherein the sound frequency pattern capturing the filtered data from the microarray is assigned using a web based sound frequency pattern generation and recognition algorithm.

6. The method of claim 1 further comprising obtaining a tissue sample from the patient for analysis.

\* \* \* \* \*